United States Patent [19]

Kishimoto et al.

[11] 4,370,332
[45] Jan. 25, 1983

[54] 1,2,3,4-TETRAHYDROISOQUINOLINE DERIVATIVES AND THE PREPARATION THEREOF

[75] Inventors: Teiji Kishimoto, Kawanishi; Hiromu Kochi, Sakai; Yoshiyuki Kaneda, Osaka, all of Japan

[73] Assignee: Fujisawa Pharmaceutical Co., Ltd., Osaka, Japan

[21] Appl. No.: 201,997

[22] Filed: Oct. 29, 1980

Related U.S. Application Data

[60] Division of Ser. No. 67,393, Aug. 17, 1979, Pat. No. 4,292,320, which is a continuation of Ser. No. 695,975, Jun. 14, 1976, abandoned, which is a continuation-in-part of Ser. No. 489,993, Sep. 19, 1974, Pat. No. 3,978,063.

[30] Foreign Application Priority Data

Jul. 30, 1973 [JP] Japan ................ 47-85987

[51] Int. Cl.³ .................. A61K 31/47; C07D 409/12
[52] U.S. Cl. .................. 424/258; 424/250; 424/251; 544/238; 544/316; 544/363; 546/148; 546/90; 546/140; 546/147; 260/155
[58] Field of Search .............. 546/148; 424/258

[56] References Cited

U.S. PATENT DOCUMENTS

| 3,378,561 | 4/1968 | Montzka | 546/148 |
| 3,389,140 | 6/1968 | Montzka | 546/148 |
| 3,389,141 | 6/1968 | Montzka | 546/148 |
| 3,437,662 | 4/1969 | Geldersteve et al. | 424/258 |
| 3,452,086 | 6/1969 | Montzka | 424/258 |
| 3,846,432 | 11/1974 | Tanaka et al. | 546/148 |
| 3,963,725 | 6/1976 | Kishimoto et al. | 546/147 |
| 4,096,263 | 6/1978 | Kishimoto et al. | 546/148 |

FOREIGN PATENT DOCUMENTS

| 2434310 | 2/1975 | Fed. Rep. of Germany . | |
| 1580899 | 9/1969 | France | 546/148 |
| 51-80867 | 7/1976 | Japan | 546/148 |
| 1032269 | 6/1966 | United Kingdom | 546/148 |

*Primary Examiner*—Donald G. Daus
*Assistant Examiner*—James H. Turnipseed
*Attorney, Agent, or Firm*—Oblon, Fisher, Spivak, McClelland & Maier

[57] ABSTRACT

A 1,2,3,4-tetrahydroisoquinoline having smooth muscle relaxant activity of the formula:

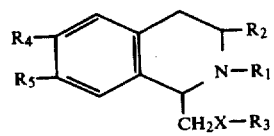

wherein $R_1$ and $R_2$ are each hydrogen or lower alkyl, $R_3$ is phenyl having substituents selected from the group consisting of lower alkenyloxy, mercapto, lower alkylthio, sulfamoyl and mono or disubstituted sulfamoyl, or a heterocyclic group, $R_4$ and $R_5$ are each hydroxy or protected hydroxy and X is —O— or —S—.

8 Claims, No Drawings

1,2,3,4-TETRAHYDROISOQUINOLINE DERIVATIVES AND THE PREPARATION THEREOF

This is a division of application Ser. No. 067,393, filed Aug. 17, 1979 now U.S. Pat. No. 4,292,320, which is a continuation of 695,975 filed June 14, 1976, now abandoned, which was a continuation-in-part of Ser. No. 489,993, filed July 19, 1974, now U.S. Pat. No. 3,978,063.

The present invention relates to new 1,2,3,4-tetrahydroisoquinoline derivatives, which have relaxing activity on smooth muscles. The present invention also relates to the preparation of new and known 1,2,3,4-tetrahydroisoquinoline derivatives.

An object of the present invention is to provide new 1,2,3,4-tetrahydroisoquinoline derivatives and their pharmaceutically acceptable salts.

The new 1,2,3,4-tetrahydroisoquinoline derivatives of the present invention are representable by the formula:

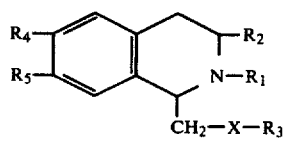

wherein $R_1$ and $R_2$ are each hydrogen or lower alkyl, $R_3$ is phenyl having substituent(s) selected from the group consisting of lower alkenyloxy, mercapto, lower alkylthio, sulfamoyl and mono or disubstituted sulfamoyl, or a heterocyclic group, $R_4$ and $R_5$ are each hydroxy or a protected hydroxy and X is —O— or —S—.

In this specification, it is to be understood that the term "lower" used in connection with the moieties derived from alkane or alkene such as alkyl or alkenyl is intended to mean a group having 1 to 6 carbon atom(s) unless otherwise indicated.

The suitable examples of lower alkyl may be one having 1 to 6 carbon atom(s), such as methyl, ethyl, propyl, isopropyl, butyl, isobutyl, t-butyl, pentyl, hexyl or the like, and preferably one having 1 to 4 carbon atom(s), and more preferably one having 1 to 2 carbon atom(s).

The suitable example of lower alkenyloxy may be one having 2 to 6 carbon atoms, such as vinyloxy, allyloxy, 1-propenyloxy, 1-isopropenyloxy, 2-butenyloxy, 3-butenyloxy, pentenyloxy, hexenyloxy or the like, and preferably one having 2 to 4 carbon atoms.

The suitable example of lower alkylthio may be one having 1 to 6 carbon atom(s), such as methylthio, ethylthio, propylthio, isopropylthio, butylthio, isobutylthio, t-butylthio, pentylthio, hexylthio or the like, and preferably one having 1 to 4 carbon atom(s), and more preferably one having 1 to 2 carbon atom(s).

The suitable example of mono or disubstituted sulfamoyl may include, for example, mono or di(lower) alkylsulfamoyl (e.g., methylsulfamoyl, ethylsulfamoyl, dimethylsulfamoyl or diethylsulfamoyl) and the like.

The heterocyclic group includes aliphatic or aromatic, saturated or unsaturated mono- or polycyclic heterocyclic groups which contain at least one hetero atom selected from the group consisting of oxygen, sulfur, nitrogen and the like. The suitable example of the heterocyclic groups may be an unsaturated 3 to 8-membered heteromonocyclic containing a sulfur atom (e.g. thienyl), an unsaturated condensed-heterocyclic containing a sulfur atom (e.g. benzothienyl), an unsaturated 3 to 8-membered heteromonocyclic containing an oxygen atom (e.g. furyl, pyranyl, 5,6-dihydro-2H-pyranyl), a saturated 3 to 8-membered heteromonocyclic containing an oxygen atom (e.g., tetrahydrofuryl, tetrahydropyranyl), an unsaturated condensed-heterocyclic containing an oxygen atom (e.g. isobenzofuranyl, chromenyl or xanthenyl), an unsaturated 3 to 8-membered heteromonocyclic containing 1 to 4 nitrogen atom(s) (e.g. 2H-pyrrolyl, 3H-pyrrolyl, pyrrolyl, pyrrolinyl, imidazolyl, pyrazolyl, pyridyl, pyrimidinyl, pyrazinyl, pyridazinyl, diazolyl, triazolyl or tetrazolyl), a saturated 3 to 8-membered heteromonocyclic containing 1 to 2 nitrogen atom(s) (e.g. pyrrolidinyl, imidazolidinyl, piperidyl or piperazinyl), an unsaturated condensed-heterocyclic containing 1 to 3 nitrogen atom(s) (e.g. indolyl, isoindolyl, indazolyl, quinolyl, isoquinolyl, benzotriazolyl or benzimidazolyl), an unsaturated 3 to 8-membered heteromonocyclic containing an oxygen atom and 1 to 3 nitrogen atom(s) (e.g. oxazolyl, isoxazolyl or oxadiazolyl), a saturated 3 to 8-membered heteromonocyclic containing 1 to 2-oxygen atom(s) and 1 to 2 nitrogen atom(s) (e.g. sydnonyl), an unsaturated condensed-heterocyclic containing an oxygen atom and 1 to 2 nitrogen atom(s) (e.g. benzoxazolyl or benzoxadiazolyl), an unsaturated 3 to 8-membered heteromonocyclic containing a sulfur atom and 1 to 3 nitrogen atom(s) (e.g. thiazolyl, isothiazolyl or thiadiazolyl), an unsaturated condensed-heterocyclic containing a sulfur atom and 1 to 2 nitrogen atom(s) (e.g. benzothiazolyl or benzothiadiazolyl), and the like, and the above illustrated heterocyclic group may have one or more appropriate substituent(s) at appropriate position of the heterocyclic ring, said substituent being, for example, lower alkyl (e.g., methyl, ethyl, propyl, isopropyl, butyl, isobutyl, tertiary-butyl, pentyl or hexyl), lower alkylthio (e.g., methylthio, ethylthio, propylthio, isopropylthio or butylthio), aryl (e.g., phenyl, tolyl or xylyl), oxo, and the like.

Suitable protective groups for hydroxy in the term "protected hydroxy" may include any of the conventional protected groups for hydroxy, for example, acyl, lower alkyl (e.g., methyl, ethyl, propyl, isopropyl, butyl, hexyl, etc.), allyl, aryl (e.g., phenyl, tolyl, xylyl, naphthyl, etc.), ar (lower) alkyl (e.g., benzyl, phenethyl, trityl, etc.), tetrahydropyranyl, methoxymethyl, 2-nitrophenylthio, 2,4-dinitrophenylthio and the like, and also include the case that $R_4$ and $R_5$ are combined together to form lower alkylenedioxy (e.g., methylenedioxy, ethylenedioxy, etc.).

A suitable example of acyl as mentioned above for the protective group for hydroxy may include:

alkanoyl having 1 to 18 carbon atom(s) such as lower alkanoyl having 1 to 6 carbon atom(s) (e.g., formyl, acetyl, propionyl, butyryl, isobutyryl, valeryl, pivaloyl, hexanoyl, etc.) and preferably one having 2 to 4 carbon atoms; or higher alkanoyl having 7 to 18 carbon atoms (e.g., heptanoyl, octanoyl, lauroyl, myristoyl, palmitoyl, stearoyl, etc.) and preferably one having 14 to 18 carbon atoms; cyclo (lower) alkanecarbonyl (e.g., cyclopropanecarbonyl, cyclobutanecarbonyl, cyclopentanecarbonyl, cyclohexanecarbonyl, etc.); lower alkenoyl (e.g., acryloyl, crotonoyl, etc.); aroyl having 7 to 11 carbon atoms (e.g. benzoyl, toluoyl, xyloyl, naphthoyl, 4-isopropylbenzoyl, etc.), and preferably one having 7 to 8 carbon atoms; lower alkoxycarbonyl having 2 to 7 carbon atoms which may be substituted with aryl, halogen or pyridyl (e.g., methoxycarbonyl, ethoxycarbonyl, 2,2,2-trichloroethoxycarbonyl, 2,2,2-tribromoethoxycarbonyl, propoxycarbonyl, 3-iodopropoxycarbonyl, isopropoxycarbonyl, butoxycarbonyl, isobutoxycarbonyl, 1,1-dimethylpropoxycarbonyl, 1-cyclopropylethoxycarbonyl, tert-butoxycarbonyl, pentyloxycarbonyl, hexyloxycarbonyl, diphenylmethoxycarbonyl, 2-pyridylmethoxycarbonyl, etc.); lower alkanesulfonyl (e.g., mesyl, ethanesulfonyl, propanesulfonyl, butanesulfonyl, hexanesulfonyl, etc.); arenesulfonyl (e.g., tosyl, benzenesulfonyl, etc.); ar (lower) alkanoyl, for example, phenyl (lower) alkanoyl having 8 to 12 carbon atoms (e.g., phenylacetyl, phenylpropionyl, phenylbutyryl, phenylhexanoyl, etc.) and preferably one having 8 to 10 carbon atoms, xylylacetyl, tolylacetyl, xylylpropionyl, etc.; aryloxy (lower) alkanoyl, for example, phenoxy (lower) alkanoyl (e.g., phenoxyacetyl, phenoxypropionyl, etc.), tolyloxyacetyl, etc.; heterocycliccarbonyl (e.g., thenoyl, nicotinoyl, isonicotinoyl, furoyl, etc.); heterocyclic (lower) alkanoyl, for example, thienyl (lower) alkanoyl (e.g., thienylacetyl, thienylpropionyl, etc.), pyridylacetyl etc., heterocyclicoxy carbonyl (e.g., 8-quinolyloxycarbonyl, etc.); 2-furfuryloxycarbonyl; higher alkoxycarbonyl (e.g., 1-adamantyloxycarbonyl, etc.); lower alkanoyl substituted with halogen (e.g., trifluoroacetyl, etc.); ar (lower) alkoxycarbonyl which may be substituted with nitro, halogen, lower alkoxy, phenylazo or lower alkoxy substituted phenylazo (e.g., benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, 4-(phenylazo)benzyloxycarbonyl, 4-(4-methoxyphenylazo) benzyloxycarbonyl, etc.) etc.

Another object of the present invention is to provide various methods for the preparation of new 1,2,3,4-tetrahydroisoquinoline derivatives (I) as well as known ones of the formula:

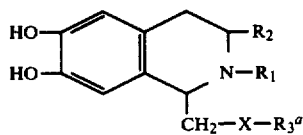
(A)

wherein $R_1$, $R_2$ and X are each as defined above, $R_3{}^a$ is phenyl having substituent(s) selected from the group consisting of hydroxy, halogen, halo(lower) alkyl, nitro, amino, mono or disubstituted amino, aryl and aryloxy.

Various methods for the preparation of the compound (I) in the present invention can be classified as follows:

1. Ring-closure from a phenethylamine structure
2. Reduction of a 3,4-dihydroisoquinoline derivative
3. Removal of a protective group on each hydroxy at the 6 and/or 7 position of the isoquinoline ring
each of which will be hereinafter illustrated in detail.

1. Ring-closure from a phenethylamine compound:
This ring-closure method is represented by the following scheme:

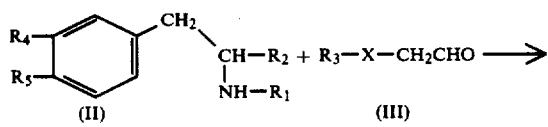

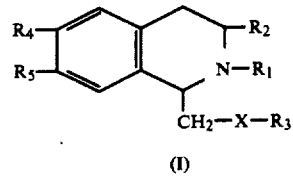
(I)

wherein $R_1$, $R_2$, $R_3$, $R_4$, $R_5$ and X are each as defined above.

In this method, the phenethylamine compound (II) is subjected to ring-closure reaction to give the object compound (I).

The ring-closure reaction is carried out by reacting the compound (II) or the salt thereof with the aldehyde compound (III) or the reactive derivative thereof.

Suitable salts of the compound (II) may include inorganic acid salt (e.g., hydrochloride, sulfate or hydrobromide) and organic acid salt (e.g., acetate, picrate, maleate or tartrate).

The reactive derivative of the aldehyde compound (III) includes all compounds convertible to the compound (III) bearing a free formyl group under reaction conditions of the ring-closure method, and compounds having equivalent workability to the compound (III) in this reaction. Suitable example of such reaction derivative may be (a) derivatives on the formyl group of the compound (III), such as acetal, hemiacetal, hydrate(-diol), mono or diacylated diol, thioacetal, hemithioacetal, Schiff's base, oxime, semicarbazone, thiosemicarbazone, alkoxalyl (e.g., methoxalyl, ethoxalyl, etc.), or the like; (b) compounds wherein the formylmethylene group of the aldehyde compound (III) is in a form of 2-acyloxyvinyl (e.g., 2-acetoxyvinyl or 2-propionyloxyvinyl), 2-lower alkoxyvinyl (e.g., 2-methoxyvinyl, 2-ethoxyvinyl, 2-propoxyvinyl or 2-isopropoxyvinyl), 2-lower alkylthiovinyl (e.g., 2-methylthiovinyl, 2-ethylthiovinyl or 2-propylthiovinyl), 2-aminovinyl, and (c) compounds substituted with the symbol Z (wherein Z is carboxy) or its derivative for one hydrogen atom on the methylene group adjacent to the formyl group of the compounds (a) or (b) mentioned above.

Suitable example of the derivative of the carboxy group for Z may be all active or inactive esters such as a saturated or unsaturated, cyclic or acyclic alkyl ester (e.g., methyl ester, ethyl ester, propyl after, isopropyl ester, butyl ester, t-butyl ester, cyclohexyl ester, cycloheptyl ester, vinyl ester, 1-propenyl ester, 2-propenyl ester, or 3-butenyl ester); an aryl ester (e.g. phenyl ester, xylyl ester, tolyl ester, or naphthyl ester); an aralkyl ester (e.g. benzyl ester or phenethyl ester) or the like; all acid amides such as amide, N-lower alkyl acid amide (e.g., N-methyl acid amide, or N-ethyl acid amide); N-phenyl acid amide; a N,N-di(lower alkyl) acid amide (e.g. N,N-dimethyl acid amide, N,N-diethyl acid amide, or N-ethyl-N-methyl acid amide); and other acid amide with imidazole, 4-substituted imidazole or the like; and acid anhydrides such as a mixed anhydride with dialkylphosphoric acid, dibenzylphosphoric acid, halogenated phosphoric acid, dialkylphosphorous acid, sulfurous acid, thiosulfuric acid, sulfuric acid, alkylcarbonic acid, an aliphatic carboxylic acid (e.g. pivalic acid, pentanoic acid, isopentanoic acid, 2-ethylbutanoic acid or chloroacetic acid), or an aromatic carboxylic acid (e.g. benzoic acid); or a symmetrical acid anhydride.

The present ring-closure reaction is preferably carried out in the presence of an acid. Suitable acid includes, for example, an inorganic acid (e.g., hydrochloric acid, sulfuric acid or hydrobromic acid) and an organic acid (e.g., acetic acid, propionic acid or picric acid). The reaction is usually carried out with or without solvent at room temperature or under warming or heating. Suitable solvent includes, for example, methanol, ethanol, n-butanol, water, benzene, chloroform, dioxane, and the like.

Some of the starting compound (II) used in the ring-closure reaction are known by Chemical Abstracts, Vol. 45(1951), column 1970d, and can be prepared by the method described therein or other analogous methods known in the arts.

2. Reduction of a 3,4-dihydroisoquinoline derivative:

This reduction method is represented by the following scheme:

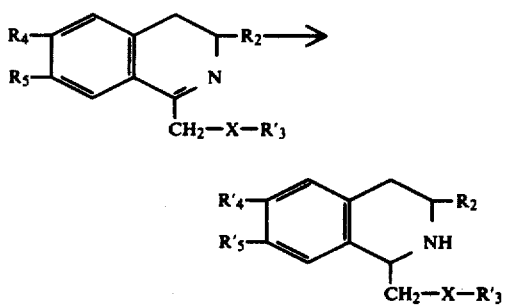

wherein $R_2$, $R_4$, $R_5$ and X are each as defined above, $R_3'$ is phenyl having substituent(s) selected from the group consisting of mercapto, lower alkylthio, sulfamoyl and mono or disubstituted sulfamoyl, or a heterocyclic group, $R_4'$ and $R_5'$ are each hydroxy or a protected hydroxy.

Thus, the 3,4-dihydroisoquinoline (IV) or the salt thereof is subjected to reduction to give the object compound (I').

Suitable salts of the compound (IV) can be referred to the ones exemplified for the compound (II) in the ring-closure reaction mentioned above.

For accomplishing the reduction of the compound (IV), there may be adopted a conventional manner known in the arts such as catalytic reduction, reduction with a reducing agent such as alkaline metal aluminum hydride or alkaline metal borohydride, and reduction with an acid and metal. It is to be understood that the reducing method employed varies depending upon a kind of the starting compounds (IV) to be employed practically.

The catalytic reduction is carried out according to a conventional manner using a conventional catalyst such as palladium carbon, Raney nickel, platinum oxide and the like, and it may be also carried out under increasing pressure. The reaction using an alkaline metal aluminium hydride is carried out according to a conventional manner in a solvent such as diethyl ether, dibutyl ether, tetrahydrofuran, dioxane or the like. Examples of suitable alkaline metal aluminium hydride may be, for example, an alkali metal aluminium hydride (e.g., lithium aluminium hydride or sodium aluminium hydride) and alkaline earth metal aluminium hydride (e.g. calcium aluminium hydride or magnesium aluminium hydride). The reaction using an acid and metal is carried out according to a conventional manner using an acid such as hydrochloric acid, sulfuric acid, acetic acid, etc. and a metal such as iron, zinc, tin or the like. The reaction using an alkaline metal borohydride is also carried out according to a conventional manner in a solvent such as water, methanol, ethanol, tetrahydrofuran, dioxane, etc. Examples of suitable alkaline metal borohydride may be, for example, an alkali metal borohydride (e.g. sodium borohydride or lithium borohydride) and alkaline earth metal borohydride (e.g., magnesium borohydride or calcium borohydride.)

When one or both of $R_4$ and $R_5$ is(are) a protected hydroxy and the protective groups are reducible groups, they may also reduced to the free hydroxy group in the course of the reduction of the compound (IV). This case is also included in the scope of this invention.

The starting compound (IV), which is novel, can be prepared, for example, by reacting a compound of the formula:

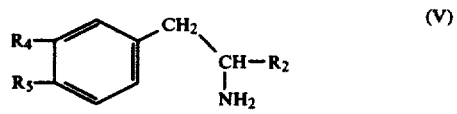

wherein $R_2$, $R_4$ and $R_5$ are each as defined above, with a compound of the formula:

$$R_3'\text{-X-CH}_2\text{-COOH} \quad (VI)$$

Wherein $R_3'$ and X are each as defined above, or the reactive derivative thereof at the carboxy group, and thereafter treating the resulting compound of the formula:

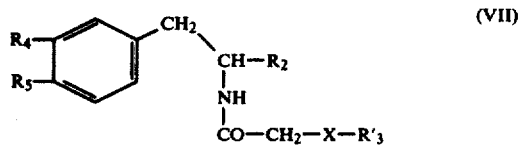

wherein $R_2$, $R_3'$, $R_4$, $R_5$ and X are each as defined above, with a dehydrating agent, or by subjecting a compound of the formula:

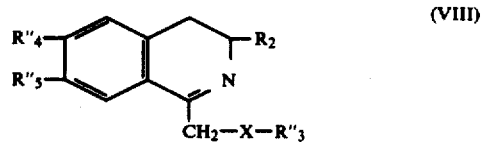

wherein $R_2$, $R_3'$ and X are each as defined above, one of $R_4''$ and $R_5''$ is protected hydroxy and the other is hydroxy or a protected hydroxy, to removal reaction of the protective group(s) on hydroxy.

3. Removal of a protective group on each hydroxy at 6 and/or 7 position of the isoquinoline ring:

The removal reaction of a protective group on each hydroxy can be represented by the following scheme:

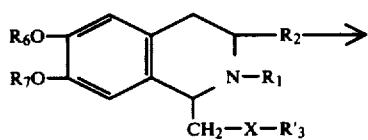

(IX)

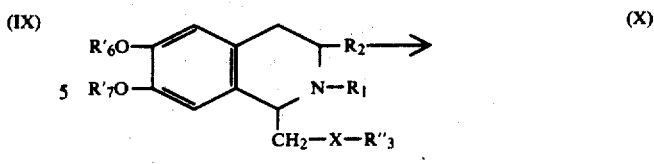

(X)

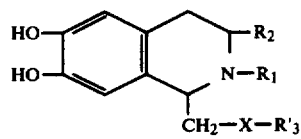

(I″)

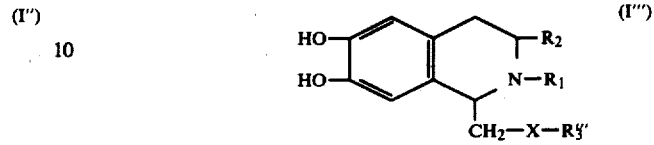

(I‴)

wherein R₁, R₂, R₃' and X are each as defined above, one of R₆ and R₇ is a protective group of hydroxy and the other is hydrogen or a protective group of hydroxy.

In this method, the compound (IX) or the salt thereof is subjected to removal reaction of the protective group of hydroxy to give the compound (I″).

Suitable salts of the compound (IX) can be referred to the ones exemplified for the compound (II) in the ring-closure mentioned above.

Examples of suitable protective group of hydroxy for R₆ and R₇ can be also referred to the ones exemplified for "protected hydroxy" for R₄ and R₅ as mentioned above.

The removal reaction of the protective groups is conducted by a conventional manner known in the arts, for example, by a hydrolysis or catalytic reduction of the compound (IX) or the salt thereof. However, it is to be understood that the reaction condition for removing the protective groups may vary depending upon a kind of the protective groups to be used. In case that protective groups are, for example, groups such as benzyl, benzyloxycarbonyl, substituted alkoxycarbonyl, adamantyloxycarbonyl, trityl, methoxymethyl, substituted phenylthio or the like, the protective groups may be removed by hydrolysis, which is carried out by treating the compound (IX) or the salt thereof with water preferably in the presence of an acid such as hydrobromic acid, hydrochloric acid, formic acid, acetic acid, trifluoroacetic acid or the like. The hydrolysis can be also carried out in a solvent such as a hydrophilic organic solvent. In case that protective groups are, for example, groups such as benzyloxycarbonyl, substituted benzyloxycarbonyl, 2-pyridylmethoxycarbonyl, diophenylmethoxycarbonyl, benzyl, trityl or the like, the protective groups may be removed by catalytic reduction, which is carried out according to a conventional manner known in the arts in the presence of a conventional catalyst such as palladium carbon or the like. In case that protective groups is trifluoroacetyl, they can be easily removed only by treating the compound (IX) or the salt thereof with aqueous alkaline solution such as sodium bicarbonate aqueous solution. It is to be understood that any other conventional methods for removing protective group on hydroxy may also be employed.

Apart from the above descriptions, the removal reaction in case that the protective group is lower alkyl is specifically given hereinafter, since new application of such removal reaction to give the known compound (A) mentioned above has been succeeded in this invention.

The removal reaction of lower alkyl protective group on hydroxy is illustrated as follows:

wherein R₁, R₂ and X are each as defined above, R₃″ is phenyl having substituent(s) selected from the group consisting of hydroxy, halogen, halo(lower)alkyl, mercapto, nitro, amino, mono or disubstituted amino, lower alkylthio, lower alkoxy, lower alkenyloxy, aryl, aryloxy, acyloxy, ar(lower)alkyloxy, sulfamoyl, mono or disubstituted sulfamoyl, and lower alkylenedioxy, or a heterocyclic group, R₃‴ is phenyl having substituent(s) selected from the group consisting of hydroxy, halogen, halo(lower)alkyl, mercapto, nitro, amino, mono or disubstituted amino, lower alkylthio, aryl, aryloxy, sulfamoyl and mono or disubstituted sulfamoyl, or a heterocyclic group and one of R₆' and R₇' is lower alkyl and the other is hydrogen or lower alkyl, or R₆' and R₇' are combined together to form lower alkylene.

Thus, the compound (X) or the salt thereof is subjected to conversion reaction of lower alkoxy to hydroxy, to give the compound (I‴).

It is understood that the compound (I‴) include both of the known compound (A) and the new compound.

Suitable salts of the compound (X) can be referred to the ones exemplefied for the compound (II) in the ring-closure.

The terms "lower alkyl", "lower alkylthio", "lower alkenyloxy", "mono or disubstituted sulfamoyl" and "a heterocyclic group", can be also referred to the exemplification given to the same groups described hereinbefore.

The term "halogen" means chlorine, bromine, fluorine or iodine.

The suitable example of halo(lower)alkyl may be one having 1 to 6 carbon atom(s), such as chloromethyl, fluoroethyl, chloropropyl, bromopropyl, iodobutyl, chloropentyl, bromochloroethyl, dichloromethyl, dichloroethyl, dibromomethyl, dibromoethyl, difluoromethyl, dichloropropyl, dichlorobutyl, dibromopropyl, difluoropropyl, difluoropropyl, trichloromethyl, tribromomethyl, trifluoromethyl, trichloroethyl, tribromoethyl or the like, and preferably one having 1 to 4 carbon atoms, and more preferably one having 1 to 2 carbon atoms.

The suitable example of mono or disubstituted amino may be, for example, mono or di(lower)alkylamino (e.g. methylamino, ethylamino, propylamino, isopropylamino, dimethylamino, diethylamino, methylethylamino, or dipropylamino), an acylamino (e.g. acetylamino, propionylamino, isopropionylamino, benzoylamino, toluoylamino, benzylcarbonylamino, p-chlorobenzoylamino, o-nitrobenzoylamino, or m-methoxybenzoylamino), an arylamino (e.g. phenylamino, o-nitrophenylanino, n-nitrophenylamino, or p-nitrophenylamino), an ar(lower) alkylamino (e.g. benzylamino, or o-bromobenzylamino), and an alkane or benzenesulfonylamino (e.g. methanesulfonylamino, ethanesulfonylamino, benzenesulfonylamino, toluenesulfonylamino, o-methoxybenzenesulfonylamino), or the like.

The suitable example of lower alkoxy may be one having 1 to 6 carbon atom(s), such as methoxy, ethoxy, propoxy, isopropoxy, butoxy, isobutoxy, t-butoxy, pentoxy, isopentoxy, hexyloxy or the like, and preferably one having 1 to 4 carbon atoms, and more preferably one having 1 to 2 carbon atoms.

The suitable example of aryl, there may be, for example, phenyl, tolyl, xylyl etc.

The suitable example of aryloxy may be, for example, phenoxy, tolyloxy, or xylyloxy.

The suitable example of acyloxy may be, for example, a lower alkanoyloxy (e.g. acetoxy, propionyloxy, isopropionyloxy or butyryloxy) and an aroyloxy (e.g. benzoyloxy, toluoyloxy, p-chlorobenzoyloxy, nitrobenzoyloxy or o-methoxybenzoyloxy), an aryloxy(or thio)carbonyloxy (e.g. phenoxycarbonyloxy or phenylthiocarbonyloxy), or an ar(lower)alkanoyloxy (e.g. benzylcarbonyloxy).

The suitable example of ar(lower)alkyloxy may be, for example, benzyloxy, tolylmethyloxy or xylylmethyloxy.

The suitable example of lower alkylenedioxy may be a lower alkylenedioxy group having 1 to 3 carbon atoms, such as methylenedioxy, dimethylmethylenedioxy, ethylenedioxy or the like.

In the above definitions, the benzene ring of aryl, aryloxy or ar(lower)alkyloxy may have substituent(s) which does not give bad influence to the present reaction such as halogen (e.g., fluorine, chlorine or bromine), nitro, lower alkoxy (e.g., methoxy or ethoxy), or the like.

For accomplishing the conversion of alkoxy for $R_6'$ and/or $R_7'$ of the compound (X) to hydroxy, can be employed all methods used conventionally for conversion of alkoxy to hydroxy in the present invention.

The methods may include, for example, a method using acid (e.g., hydrochloric acid or hydrobromic acid), boron trihalide (e.g., boron trichloride or boron tribromide), aluminum chloride, pyridine hydrochloride, lithium iodide, lithium tertiary-butyl sulfide and a mixture thereof, and the like, and when liquid form of those are used in the present reaction, the reaction can be carried out without solvent. Methylene chloride is often used as solvent, but other any solvent which does not give bad influence to the present reaction can be used in the present invention.

There is no particular limitation to the reaction temperature, and it is suitably selected according to a kind of reagents, solvents, and the like.

In the course of the conversion, some of substituent(s) on the phenyl group for $R_3''$ may be removable, too, and such case is also included in the scope of this invention.

According to the removal reaction of the compound (X) to the compound (I'''), can be prepared the compound (I''') more economically, since cheaply and commercially available starting raw materials for the preparation of the compound (X), such as vanillin can be employed as they are without previous modification.

Among the starting compounds used in the removal reaction, the compound (IX), and some of the compound (X) are novel and the other of the compound (X) is known, for example, according to Collection of Czechoslovakian Chemical Communication, Vol. 32 (1967), page 1197, and can be prepared by the method described therein. The novel starting compounds can be prepared, for example, by reducing the corresponding same type compounds as the compound (IV), whose preparation is also illustrated above. 4. Removal of a protective group for imino at the 2 position of the isoquinoline ring.

The removal reaction of a protective group for imino can be represented by the following scheme:

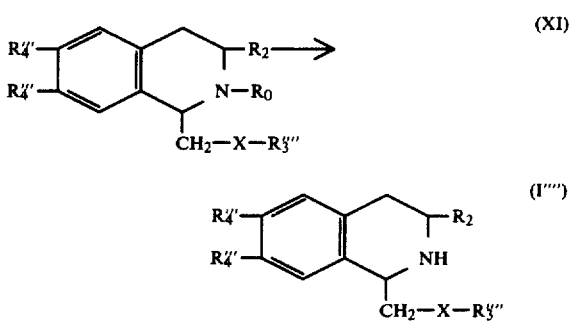

wherein $R_2$ and X are each as defined above, $R_3''''$ is a heterocyclic group, $R_4'''$ is acyloxy and $R_5$ is a protective group for imino.

In this method, the compound (XI) is subjected to removal reaction of the protective group for imino to give the compound (X'''').

Suitable heterocyclic group for $R_5''''$ can be referred to the ones as exemplified hereinbefore.

Suitable acyl in the term "acyloxy" for $R_4'''$ can be referred to the ones as exemplified hereinbefore. The acyloxy groups for $R_4'''$ at the 6 and 7 position of the isoquinoline ring may be same or different.

Suitable protective group for imino for $R_5$ may include any of the conventional protective groups for imino which can be removed by the present reaction, for example, easily removable acyl such as mono (or di or tri) halo (lower) alkanoyl (e.g., chloroacetyl, dichloroacetyl, trichloroacetyl, trifluoroacetyl, etc.), mono (or di or tri) halo (lower) alkoxycarbonyl (e.g., trichloroethoxycarbonyl, tribromoethoxycarbonyl, iodopropoxycarbonyl, etc.), tertiary-butoxycarbonyl, tertiary-pentyloxycarbonyl, 1-cyclopropylethoxycarbonyl, 1-adamantyloxycarbonyl, heterocyclioooxycarbonyl (e.g., 5-quinolyloxycarbonyl, etc.), 2-furfuryloxycarbonyl or substituted or unsubstituted ar(lower)alkoxycarbonyl (e.g., benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, etc.), ar(lower)alkyl (e.g., benzyl, trityl, etc.) etc.

The removal reaction of the protective group for imino is conducted by a conventional manner known in the arts, for example, by a hydrolysis or reduction of the compound (XI) according to a kind of the protective group for imino).

The removal reaction by hydrolysis is carried out by treating the compound (XI) with water preferably in the presence of an acid such as hydrochloric acid, formic acid, acetic acid, trifluoroacetic acid or the like. In this case, the acid is preferably used in its diluted form. The hydrolysis can be also carried out in a solvent such as a hydrophilic organic solvent.

The removal reaction by reduction is carried out by a method using a combination of metal (e.g., tin, zinc, etc.) or metallic compound (e.g., chromous chloride, chromous acetate, etc.) and acid such as organic acid (e.g., formic acid, acetic acid, propionic acid, etc.) or inorganic acid (e.g., hydrochloric acid, etc.) or by catalytic reduction. Suitable catalyst may include conventional catalyst such as palladium carbon or the like. Any other conventional methods for removing protective group for imino may be also employed.

The reaction temperature is not restrictive and is optionally selected according to a kind of the protective group, the removal method to be used etc.

The starting compound (XI) can be prepared, for example, by subjecting a compound of the formula:

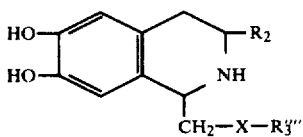

(XII)

wherein $R_2$, $R_3''''$ and X are each as defined above, to introduction reaction of protective group for imino, and thereafter acylating the resulting compound of the formula:

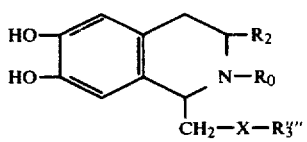

(XIII)

wherein $R_2$, $R_3''''$, $R_4$ and X are each as defined above.

The introduction reaction of protective group for imino is carried out by conventional methods, for example, by reacting a compound (XII) with a compound of the formula: $R_4'$—OH (XIV) wherein $R_4'$ is easily removable acyl, or reactive derivative thereof at the carboxy group when the protective group is easily removable acyl or by reacting a compound (XII) with a compound of the formula: $R_4''$—Y (XV) wherein $R_4''$ is ar(lower)alkyl and Y is an acid residue when the protective group is ar(lower)alkyl.

Suitable example of easily removable acyl for $R_4'$ can be referred to the ones as exemplified hereinbefore.

The suitable reactive derivatives at the carboxy group of the compound (XIV) may include, for example, an acid halide, an acid anhydride, an activated amide, an activated ester, and preferably an acid chloride; an acid azide; a mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid, trichloroacetic acid, etc.), aromatic carboxylic acid (e.g., benzoic acid, etc.), or a symmetrical acid anhydride; an acid amide with imidazole, 4-substituted imidazole, dimethylpyrazole, triazole or tetrazole; or an ester (e.g., cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), or the like. The suitable reactive derivative can be optionally selected from them according to the kind of the compound (XIV) to be used practically.

Suitable example of acid residue for Y may include halogen (e.g., chlorine, bromine, etc.), arenesulfonyloxy (e.g., benzenesulfonyloxy, tosyloxy, etc.), etc.

The reaction of the compound (XII) with the compound (XIV) or reactive derivative thereof at the carboxy group is usually carried out in a solvent such as water, acetone, dioxane, acetonitrile, chloroform, methylene chloride, ethylene chloride, tetrahydrofuran, ethyl acetate, dimethylformamide, pyridine or any other organic solvent which does not adversely affect the reaction. Amont these solvents, hydrophilic solvents may be used in a mixture with water.

When the compound (XIV) is used in a form of the free acid or salt in this reaction, the reaction is preferably carried out in the presence of a condensing agent such as N,N'-dicyclohexylcarbodiimide, N-cyclohexyl-N'-morpholinoethylcarbodiimide, N-cyclohexyl-N'-(4-diethylaminocyclohexyl) carbodiimide, N,N'-diethylcarbodiimide, N,N'-diisopropylcarbodiimide, N-ethyl-N'-(3-dimethylaminopropyl)-carbodiimide, N,N'-carbonyldi(2-methylimidazole),pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, N-ethyl-benzisoxazolium salt, N-ethyl-5-phenyl-isoxazolium-3'-sulfonate, Vilsmeier reagent such as (chloromethylene)dimethylammonium chloride or the like, or the like.

Also, the reaction may be carried out in the presence of a base, for example, an inorganic base such as alkali metal hydroxide (e.g., sodium hydroxide, potassium hydroxide, etc.), alkali metal bicarbonate (e.g., sodium bicarbonate, potassium bicarbonate, etc.) or alkali metal carbonate (e.g., sodium carbonate, etc.); or an organic base such as trialkylamine (e.g., trimethylamine, triethylamine, etc.), N,N-dialkylbenzylamine, N,N-dialkylaniline or pyridine. When the base or the condensing agent is in liquid, it can also be used as a solvent. The reaction temperature is not critical, and the reaction is preferably carried out under cooling.

The reaction of the compound (XII) with the compound (XV) is usually carried out in a solvent in the presence of a base.

Thus obtained compound (XIII) is thereafter acylated to give the compound (XI).

The present acylation reaction is carried out by reacting the compound (XIII) with an acylating agent.

The acylating agent to be used for the present reaction may be a compound of the formula: $R_4'''$—H (XVI) wherein $R_4'''$ is as defined above, or reactive derivative thereof.

A suitable reactive derivative of the compound (XVI) can be referred to the ones exemplified for the compound (XIV).

The present reaction is carried out according to similar reaction conditions to those of aforesaid reaction of the compound (XII) with the compound (XIV). In this case, the reaction is usually carried out at any temperature from cooling to heating.

The desired compounds (I) and (A) obtained by the above methods may be, if necessary, converted into its pharmaceutically acceptable salt with an acid, such as an inorganic acid (e.g., hydrochloric acid, hydrobromic acid or sulfuric acid) or an organic acid (e.g., acetic acid, tartaric acid or picric acid).

The new 1,2,3,4-tetrahydroisoquinoline derivatives (I) of the present invention and the pharmaceutically acceptable salts thereof have relaxing activity on smooth muscles, especially on vascular-and visceral-smooth muscles. Accordingly, they show vasodilating, intestinal-contraction inhibiting and bladder-contraction inhibiting activities, showing less bronchodilating activity, and are useful as vasodilating, intestinal-contraction inhibiting and bladder-contraction inhibiting agents. Thus, the compound (I) of the present invention and the pharmaceutically acceptable salts thereof can be used as a medicine for treating spasmodic disorder of visceral organs, e.g., colonic irritability, chronic cholecystitics, etc.

The new 1,2,3,4-tetrahydroisoquinoline derivatives (I) and the pharmaceutically acceptable salts thereof can be administered by the conventional methods, the conventional types of unit dosages or with the conventional pharmaceutical carriers to produce relaxing activities on smooth muscles of domestic animals.

Thus, they can be used in the form of pharmaceutical preparations, which contain them in admixture with a pharmaceutical organic or inorganic carrier material suitable for enteral or parenteral applications. Oral administration by the use of tablets, capsules or in liquid form such as suspensions, solutions or emulsions is particularly advantageous. When formed into tablets, the conventional binding and disintegrating agents used in therapeutic unit dosages can be employed. Illustrative of binding agents there can be mentioned glucose, lactose, gum acacia, gelatin, mannitol, starch paste, magnesium trisilicate and talc. Illustrative of disintegrating agents there can be mentioned corn starch, keratin, colloidal silica and potato starch. When administered as liquids the conventional liquid carriers can be used.

The unit dosage or therapeutically effective quantity of the compounds (I) and the pharmaceutically acceptable salts thereof for human beings can vary over wide limits such as that of 0.01 milligram to about 100 milligrams. The upper limit is limited only by the degree of effect desired and economical considerations. For oral administration it is preferable to employ from about 1 milligram to about 100 milligrams of the therapeutic agent per unit dosage. It is indicated from animal experiments that about 0.1 to about 10 milligrams dosages administered orally three times daily as needed will provide a preferred daily dosage. Of course, the dosage of the particular therapeutic agent used can vary considerably, such as the age of the patient and the degree of therapeutic effect desired. Each unit dosage form of the novel therapeutic compounds can contain from about 0.05 to about 99.5% of the novel therapeutic agents by weight of the entire composition with the remainder comprising conventional pharmaceutical carriers. By the term pharmaceutical carrier it is intended to include non-therapeutic materials which are conventionally used with unit dosage and include fillers, diluents, binders, lubricants, disintegrating agents and solvents. Of course, it is possible to administer the novel therapeutics, i.e. the pure compounds, without the use of a pharmaceutical carrier. It is also possible to administer the new 1,2,3,4-tetrahydroisoquinoline derivatives (I) and the pharmaceutically acceptable salts thereof in the form of mixture with other agents which are used as a relaxant on smooth muscles and especially on vascular-smooth and visceral-smooth muscles.

Practical and presently-preferred embodiments of this invention shown in the following Examples.

EXAMPLE 1

(A) A solution of 3,4-dihydroxyphenethylamine hydrochloride (3.3 g) and (4-allyloxyphenoxy)acetaldehyde diethyl acetal (5.2 g) in a mixture of n-butanol (45 ml), water (12 ml) and concentrated hydrochloric acid (2 drops) was refluxed for 4 hours. After the reaction, the reaction mixture was concentrated to dryness. The residue was crystallized by adding acetone, and the crystals were recrystallized from a mixed solvent of 99% ethanol and ether to give 1-(4-allyloxyphenoxy)-methyl-6,7-dihydroxy-1,2,3,4-tetrahydroisoquinoline hydrochloride (6.0 g), mp 114° to 116° C.

Analysis: $C_{19}H_{21}NO_4 \cdot HCl$: Calcd.: C: 62.72, H: 6.10, N: 3.85, Cl: 9.74. Found: C: 62.52, H: 6.37, N: 3.91, Cl: 9.65.

(B) To a mixture of n-butanol (10 ml), water (2.5 ml) and concentrated hydrochloric acid (1 drop) were added 3,4-dihydroxyphenethylamine hydrochloride (0.63 g) and (4-methylthiophenoxy)acetaldehyde diethyl acetal (1.0 g), and the mixture was refluxed for 5 hours. After the reaction, the reaction mixture was concentrated to dryness under reduced pressure. The residue was crystallized by adding acetone, and the crystals were recrystallized from a mixture solvent of methanol and ether to give 1-(4-methylthiophenoxy)-methyl-6,7-dihydroxy-1,2,3,4-tetrahydroisoquinoline hydrochloride (1.2 g), mp 270° C. (dec.).

Analysis: $C_{17}H_{19}NO_3S \cdot HCl$: Calcd.: C: 57.70, H: 5.70, N: 3.96, Cl: 10.02. Found: C: 57.30, H: 5.65, N: 3.82, Cl: 10.27.

(C) To a mixture of acetic acid (23 ml), water (6.6 ml) and concentrated hydrochloric acid (15 drops) was added (4-sulfamoylphenoxy)acetaldehyde diethyl acetal (2.3 g), and the mixture was heated for 20 minutes at 110° C. To the solution was added 3,4-dihydroxyphenethylamine hydrochloride (1.2 g), and the mixture was heated for 3.5 hours at the same temperature. After the reaction, the reaction mixture was concentrated to dryness under reduced pressure. The residue was crystallized by adding acetone, and the crystals were recrystallized from a mixed solvent of methanol and acetone to give 1-(4-sulfamoylphenoxy)methyl-6,7-dihydroxy-1,2,3,4-tetrahydroisoquinoline hydrochloride (1.8 g), mp 270° C. (dec.).

Analysis: $C_{16}H_{18}N_2O_5S \cdot HCl$: Calcd.: C: 49.68, H: 4.95, N: 7.24, S: 8.29. Found: C: 49.58, H: 4.95, N: 7.01, S: 8.31.

(D) The following compound was obtained by using the similar procedure to those of the above examples 1 (A) to 1 (C).

1-(4-allyloxyphenyl)thiomethyl-6,7-dihydroxy-1,2,3,4-tetrahydroisoquinoline hydrochloride, mp 191° to 193° C.

Analysis: $C_{19}H_{21}NO_3S \cdot HCl$: Calcd.: C: 60.07, H: 5.84, N: 3.69, S: 8.44, Cl: 9.33. Found: C: 60.03, H: 5.75, N: 3.75, S: 8.47, Cl: 9.60.

(E) A mixture of 3,4-dihydroxyphenethylamine hydrochloride (3.9 g), (2-pyrimidinyl)thioacetaldehyde diethyl acetal (6.1 g), n-butanol (78 ml), water (39 ml)

and 10% hydrochloric acid (2 drops) was stirred for 45 minutes at 80° C. and for 1.5 hours at 90° C. After the reaction, n-butanol was distilled off from the reaction mixture under reduced pressure. The residue was dissolved in water, and the solution was treated with activated charcoal powder and then washed three times with chloroform and once with ether. The aqueous layer was concentrated to a volume of about 15 ml. The precipitates were collected by filtration and washed with water and then recrystallized from aqueous methanol to give colourless needles of 1-(2-pyrimidinyl)thiomethyl-6,7-dihydroxy-1,2,3,4-tetrahydroisoquinoline hydrochloride, mp 204° to 205° C. (dec.).

Analysis: $C_{14}H_{15}O_2N_3S.HCl.H_2O$: Calcd.: C: 48.90, H: 5.28, N: 12.22, S: 9.33, Cl: 10.31. Found: C: 48.82, H: 5.10, N: 12.13, S: 9.67, Cl: 10.37.

(F) A mixture of 3,4-dihydroxyphenethylamine hydrochloride (4.42 g), (5-methyl-4H-1,2,4-triazol-3-yl)thioacetaldehyde diethyl acetal (6.5 g), n-butanol (88 ml), water (44 ml) and 10% hydrochloric acid (4 drops) was refluxed for 19 hours. After the reaction, n-butanol was distilled off from the reaction mixture under reduced pressure. The residue was dissolved in water, and the solution was washed three times with chloroform and once with ether. The aqueous layer was concentrated under reduced pressure. The oily residue was dissolved in methanol (10 ml) and then crystallized by adding acetone. The crystals were collected by filtration and dried to give colourless crystals of 1-(5-methyl-4H-1,2,4-triazol-3-yl)thiomethyl-6,7-dihydroxy-1,2,3,4-tetrahydroisoquinoline hydrochloride (5.9 g), mp 224° to 225° C. (dec). The product was recrystallized by aqueous methanol to give colourless plates, mp 229° to 231° C.

Analysis: $C_{13}H_{16}O_2N_4S.HCl.\frac{1}{2}H_2O$: Calcd.: C: 46.21, H: 5.37, N: 16.58, S: 9.50, Cl: 10.50. Found: C: 46.59, H: 5.41, N: 16.35, S: 9.28, Cl: 10.68.

(G) A mixture of 3,4-dihydroxyphenethylamine hydrochloride (5 g), (2-thienyl)thioacetaldehyde diethyl acetal (9.2 g), n-butanol (100 ml), water (50 ml) and concentrated hydrochloric acid (5 drops) was refluxed for 20 hours. After the reaction, n-butanol was distilled off from the reaction mixture under reduced pressure. The residue was dissolved in water and the solution was washed five times with chloroform and once with ether, and then aqueous layer was concentrated. The oily residue was crystallized by adding methanol and acetone, and the crystals were recrystallized from aqueous acetone to give prism crystals of 1-(2-thienyl)thiomethyl-6,7-dihydroxy-1,2,3,4-tetrahydroisoquinoline hydrochloride, mp 177° to 178° C.

Analysis: $C_{14}H_{15}O_2NS_2.HCl$: Calcd.: C: 50.97, H: 4.89, N: 4.25, S: 19.44, Cl: 10.75. Found: C: 51.00, H: 4.88, N: 4.14, S: 19.02, Cl: 10.67.

(H) A mixture of 3,4-dihydroxyphenethylamine hydrochloride (6.5 g), (5-methyl-1,3,4-thiadiazol-2-yl)thioacetaldehyde diethyl acetal (12.7 g), n-butanol (130 ml), water (65 ml) and 10% hydrochloric acid (6 drops) was refluxed for 20 hours. After the reaction, n-butanol was distilled off from the reaction mixture under reduced pressure. The residue was dissolved in water and the solution was washed three times with chloroform and once with ether. The aqueous layer was concentrated, and the oily residue was crystallized by adding methanol and acetone. The crystals were collected by filtration and recrystallized from a mixture of methanol and acetone to give 1-(5-methyl-1,3,4-thiadiazol-2-yl)thiomethyl-6,7-dihydroxy-1,2,3,4-tetrahydroisoquinoline dihydrochloride, mp 199° to 201° C. (dec.).

Analysis: $C_{13}H_{15}O_2N_3S_2.2HCl.\frac{1}{2}H_2O$. Calcd.: C: 39.98, H: 4.64, N: 10.74, S: 16.39, Cl: 18.12. Found: C: 40.04, H: 4.50, N: 10.41, S: 16.47, Cl: 18.28.

(I) A mixture of 3,4-dihydroxyphenethylamine hydrochloride (2.4 g), (4-pyridyl)oxyacetaldehyde diethyl acetal (3.7 g), n-butanol (40 ml) and 1 N-hydrochloric acid (20 ml) was refluxed for 15 hours under stirring. After the reaction, n-butanol was distilled off from the reaction mixture under reduced pressure. The residue was dissolved in water, and the solution was washed twice with chloroform and once with ether. The aqueous layer was concentrated, and the oily residue was allowed to stand to give crystals of 1-(4-pyridyl)oxymethyl-6,7-dihydroxy-1,2,3,4-tetrahydroisoquinoline dihydrochloride (4.7 g). The product was recrystallized from aqueous methanol to give needles, mp 250° to 255° C. (dec.).

Analysis: $C_{15}H_{16}O_3H_2.2HCl.4/5H_2O$. Calcd.: C: 50.09, H: 5.40, N: 7.79, Cl: 19.72. Found: C: 50.34, H: 5.48, N: 7.83, Cl: 19.33.

(J) A mixture of 3,4-dihydroxyphenethylamine hydrochloride (1.62 g), (1,2,5-thiadiazol-3-yl)oxyacetaldehyde diethyl acetal (2.6 g), n-butanol (50 ml), water (25 ml) and 10% hydrochloric acid (3 drops) was refluxed for 15 hours. After the reaction, n-butanol was distilled off from the reaction mixture under reduced pressure. The residue was dissolved in water, and the solution was washed twice with chloroform and once with ether and then the aqueous layer was concentrated to give colourless crystals of 1-(1,2,5-thiadiazol-3-yl)oxymethyl-6,7-dihydroxy-1,2,3,4-tetrahydroisoquinoline hydrochloride (2 g). The product was recrystallized from aqueous methanol to give colourless crystals like cotton, mp 252° C. (dec.).

Analysis: $C_{12}H_{13}O_3N_3S.HCl$. Calcd.: C: 45.64, H: 4.47, N: 13.31, S: 10.15, Cl: 11.23. Found: C: 45.41, H: 4.24, N: 13.10, S: 10.19, Cl: 11.27.

(K) A mixture of 3,4-dihydroxyphenethylamine hydrochloride (8.35 g), (1,3,4-thiadiazol-2-yl)thioacetaldehyde diethyl acetal (15.5 g), n-butanol (160 ml), water (80 ml) and 10% hydrochloric acid (10 drops) was refluxed for 24 hours. After the reaction, n-butanol was distilled off from the reaction mixture under reduced pressure. The residue was dissolved in water, and the solution was washed twice with chloroform and once with ether. The aqueous layer was concentrated, and the oily residue was crystallized by adding methanol and acetone. The crystals were collected by filtration and dried to give 1-(1,3,4-thiadiazol-2-yl)thiomethyl-6,7-dihydroxy-1,2,3,4-tetrahydroisoquinoline hydrochloride. The product was recrystallized from aqueous methanol to give faint yellow granular crystals, mp 234° C. (dec).

Analysis: $C_{12}H_{13}O_2N_3S_2.HCl$. Calcd.: C: 43.43, H: 4.25, N: 12.66, S: 19.33, Cl: 10.68. Found: C: 43.32, H: 4.18, N: 12.43, S: 19.10, Cl: 10.89.

(L) A mixture of 3,4-dihydroxyphenethylamine hydrochloride (2.86 g), (1-methyl-1H-tetrazol-5-yl)-thioacetaldehyde diethyl acetal (5.2 g), n-butanol (57 ml), water (28 ml) and 10% hydrochloric acid (5 drops) was refluxed for 18 hours. After the reaction, n-butanol was distilled off from the reaction mixture under reduced pressure. The residue was dissolved in water, and the solution was washed twice with chloroform and once with ether, and then the aqueous layer was concentrated to give clourless crystals of 1-(1-methyl-1H-tetrazol-5-yl)thiomethyl-6,7-dihydroxy-1,2,3,4-tetrahydroisoquinoline hydrochloride (3.7 g). The product was recrystallized from a mixture of methanol and ether to give colourless crystals, mp 215° to 216° C. (dec.).

Analysis: $C_{12}H_{15}O_2N_5S \cdot HCl \cdot H_2O$. Calcd.: C: 41.44, H: 5.22, N: 20.14, S: 9.22, Cl: 10.19. Found: C: 41.63, H: 5.13, N: 19.90, S: 9.37, Cl: 10.34.

(M) A mixture of 3,4-dihydroxyphenethylamine hydrochloride (2.14 g), (2-benzothiazolyl)thioacetaldehyde diethyl acetal (4.8 g), n-butanol (75 ml) and water (10 ml) was refluxed for 3 hours. After the reaction, n-butanol was distilled off from the reaction mixture under reduced pressure. To the residue were added water (10 ml) and ethyl acetate (40 ml), and the mixture was vigorously stirred. The precipitated powder was collected by filtration and washed with acetone and recrystallized from a mixture of 95% ethanol (30 ml) and ether (30 ml) to give 1-(2-benzothiazolyl)thiomethyl-6,7-dihydroxy-1,2,3,4-tetrahydroisoquinoline hydrochloride, mp 170° to 172° C.

(N) The following compounds were obtained by using the similar procedure those of the above examples 1 (E) to 1 (M).

(1) 1-(2-oxotetrahydrofuran-3-yl)thiomethyl-6,7-dihydroxy-1,2,3,4-tetrahydroisoquinoline hydrochloride, mp 236° to 239° C. (dec.).

(2) 1-(1-methyl-1H-tetrazol-5-yl)thiomethyl-6,7-dibenzyloxy-1,2,3,4-tetrahydroisoquinoline, mp 106° to 108° C.

(3) 1-(1-methyl-1H-tetrazol-5-yl)thiomethyl-6,7-dimethoxy-1,2,3,4-tetrahydroisoquinoline, mp 96° to 99° C.

Preparation of the starting compounds (1)-(3)

(1) 1-(1-methyl-1H-tetrazol-5-yl)thiomethyl-6,7-dibenzyloxy-3,4-dihydroisoquinoline (i) N-(3,4-dibenzyloxyphenethyl)-(1-methyl-1H-tetrazol-5-yl)thioacetamide To a suspension of (1-methyl-1H-tetrazol-5-yl)thioacetic acid (10 g) in dried benzene (100 ml) were added a solution of thionyl chloride (10.2 g) in dried benzene (30 ml) and dimethylformamide (1 drop) in turn at room temperature, and the mixture was refluxed for 1 hour. After the reaction, the solvent was distilled off to give crystals of (1-methyl-1H-tetrazol-5-yl)thioacetyl chloride. To a solution of 3,4-dibenzyloxyphenethylamine (9.3 g) in a mixture of dried benzene (90 ml) and dried chloroform (10 ml) was firstly added triethylamine (3.66 g) and then was dropwise added over 20 minutes under stirring and ice cooling a solution of the above obtained (1-methyl-1H-tetrazol-5-yl)-thioacetyl chloride in a mixture of dried benzene (50 ml) and dried chloroform (5 ml). The mixture was stirred for 30 minutes at the same temperature and for 30 minutes at room temperature. The solvent was distilled off and the residue was dissolved in chloroform. The solution was in turn washed with 5% hydrochloric acid, water, dilute sodium bicarbonate aqueous solution and water and dried. The solvent was distilled off and the residue was crystallized from ether to give N-(3,4-dibenzyloxyphenethyl)-(1-methyl-1H-tetrazol-5-yl)-thioacetamide (10.7 g), mp 110° C.

(ii) 1-(1-methyl-1H-tetrazol-5-yl)thiomethyl-6,7-dibenzyloxy-3,4-dihydroisoquinoline A mixture of N-(3,4-dibenzyloxyphenethyl)-(1-methyl-1H-tetrazol-5-yl)thioacetamide (9.6 g), phosphorus oxychloride (3.23 g) and dried acetonitrile (100 ml) was refluxed for 2.5 hours. The solvent was distilled off and to the residue was added a mixture of chloroform and water. The mixture was alkalified by adding aqueous ammonia solution and then extracted with chloroform. The extract was washed with water, dried and the solvent was distilled off. The residue was crystallized by treating with ether and the crystals were recrystallized from a mixture of ethyl acetate and ether to give 1-(1-methyl-1H-tetrazol-5-yl)thiomethyl-6,7-dibenzyloxy-3,4-dihydroisoquinoline (6 g), mp 146° to 148° C.

(2) 1-(1-methyl-1H-tetrazol-5-yl)thiomethyl-6,7-dihydroxy-3,4-dihydroisoquinoline hyrochloride A mixture of 1-(1-methyl-1H-tetrazol-5-yl)-thiomethyl-6,7-dibenzyloxy-3,4-dihydroisoquinoline (1 g), 99% ethanol (10 ml) and concentrated hydrochloric acid (10 ml) was refluxed for 3 hours. After the reaction the solvent was distilled off and the residue was crystallized from a mixture of isopropanol and ether to give 1-(1-methyl-1H-tetrazol-5-yl)thiomethyl-6,7-dihydroxy-3,4-dihydroisoquinoline hydrochloride (0.75 g), mp 130° C. (dec.).

(3) 1-(1-methyl-1H-tetrazol-5-yl)thiomethyl-6,7-dimethoxy-3,4-dihydroisoquinoline (i) N-(3,4-dimethoxyphenethyl)-(1-methyl-1H-tetrazol-5-yl)thioacetamide A solution of (1-methyl-1H-tetrazol-5-yl)-thioacetic acid (10 g) and thionyl chloride (10.2 g) in a mixture of dried benzene (130 ml) and dimethylformamide (1 drop) was warmed for 1.5 hours at 50° C. The solvent was distilled off and dried benzene was added to the residue. Excess thionyl chloride was removed by evaporating benzene to give crystals of (1-methyl-1H-tetrazol-5-yl)-thioacetyl chloride. A solution of the above obtained acid chloride in a mixture of dried benzene (70 ml) and dried chloroform (7 ml) was dropwise added over 30 minutes under stirring and ice cooling to a solution of 3,4-dimethoxyphenethylamine (8.0 g) and triethylamine (5.80 g) in a mixture of dried benzene (120 ml) and dried chloroform (15 ml). The mixture was stirred for 1 hour at the same temperature and further 1 hour at room temperature, after which the solvent was removed. The residue was dissolved in ethyl acetate and the solution was in turn washed with water, 5% hydrochloric acid, water, dilute sodium bicarbonate aqueous solution and water, and dried. The solvent was distilled off and the residual oil was crystallized by treating with ether. The crystals were collected by filtration and washed with ether to give N-(3,4-dimethoxyphenethyl)-(1-methyl-1H-tetrazol-5-yl)thioacetamide (9.7 g). The crystals were recrystallized from a mixture of ethyl acetate and ether to give colorless crystals of the object compound, mp 90° to 92° C.

(ii) 1-(1-methyl-1H-tetrazol-5-yl)thiomethyl-6,7-dimethoxy-3,4-dihydroisoquinoline A mixture of N-(3,4-dimethoxyphenethyl)-(1-methyl-1H-tetrazol-5-yl)thioacetamide (9 g), phosphorus oxychloride (4.5 g) and dried acetonitrile (90 ml) was refluxed for 3 hours and 20 minutes. The solvent was removed and 10% hydrochloric acid (100 ml) was added to the residue. The solution was washed with ethyl acetate, alkalified under ice-cooling by aqueous ammonia and extracted with chloroform. The extract was washed with water, dried and concentrated. The residual crystals were washed with ether to give 1-(1-methyl-1H-tetrazol-5-yl)-thiomethyl-6,7-dimethoxy-3,4-dihydroisoquinoline (6.6 g). The crystals were recrystallized from a mixture of ethanol and ether to give colorless crystals of the object compound, mp 162° to 164° C.

EXAMPLE 2

(A) To a suspension of 1-(1-methyl-1H-tetrazol-5-yl)-thiomethyl-6,7-dibenzyloxy-3,4-dihydroisoquinoline (1 g) in methanol (10 ml) was added sodium borohydride (120 mg), and the mixture was stirred for 1.5 hours at room temperature. After the reaction precipitated crystals were collected by filtration and washed with methanol to give 1-(1-methyl-1H-tetrazol-5-yl)thiomethyl-6,7-dibenzyloxy-1,2,3,4-tetrahydroisoquinoline (0.88 g). This crystals were recrystallized from ethanol to give crystals, mp 106° to 108° C.

(B) 1-(1-methyl-1H-tetrazol-5-yl)thiomethyl-6,7-dihydroxy-3,4-dihydroisoquinoline hydrochloride (0.2 g) was dissolved in methanol (5 ml) under warming. To the solution was added sodium borohydride (50 mg) and the mixture was stirred for 1.5 hours at room temperature. 10% Hydrochloric acid was added to the reaction mixture and the solution was concentrated. Dried methanol was added to the residue and the insoluble material was filtered off, after which the filtrate was evaporated. The residue was crystallized by treating with acetone to give 1-(1-methyl-1H-tetrazol-5-yl)thiomethyl-6,7-dihydroxy-1,2,3,4-tetrahydroisoquinoline hydrochloride (0.16 g), mp 215° to 216° C. (dec.).

(C) To a mixture of 1-(1-methyl-1H-tetrazol-5-yl)-thiomethyl-6,7-dimethoxy-3,4-dihydroisoquinoline (3.2 g) and ethanol (30 ml) was added sodium borohydride (400 mg), and the mixture was warmed for 2 hours at 50° C. The solvent was distilled off, and the residue was extracted by adding chloroform. The extract was washed with water, dried and concentrated. The residue was crystallized by treating with ether and the crystals were collected by filtration and washed with ether to give 1-(1-methyl-1H-tetrazol-5-yl)thiomethyl-6,7-dimethoxy-1,2,3,4-tetrahydroisoquinoline (2.7 g). The crystals were recrystallized from a mixture of ethyl acetate and ether to give crystals of the object compound, mp 96° to 99° C.

(D) The following compounds were obtained by using the similar procedure to those of the above examples, 2 (A) to 2 (C).

(1) 1-(2-pyrimidinyl)thiomethyl-6,7-dihydroxy-1,2,3,4-tetrahydroisoquinoline hydrochloride, mp 204° to 205° C. (dec.).

(2) 1-(5-methyl-4H-1,2,4-triazol-3-yl)thiomethyl-6,7-dihydroxy-1,2,3,4-tetrahydroisoquinoline hydrochloride, mp 229° to 231° C. (dec.)

(3) 1-(2-thienyl)thiomethyl-6,7-dihydroxy-1,2,3,4-tetrahydroisoquinoline hydrochloride, mp 177° to 178° C.

(4) 1-(5-methyl-1,3,4-thiadiazol-2-yl)thiomethyl-6,7-dihydroxy-1,2,3,4-tetrahydroisoquinoline dihydrochloride, 199° to 201° C. (dec.).

(5) 1-(4-byridyl)oxymethyl-6,7-dihydroxy-1,2,3,4-tetrahydroisoquinoline dihydrochloride, mp 250° to 255° C. (dec.).

(6) 1-(1,2,5-thiadiazol)-3-yl)oxymethyl-6,7-dihydroxy-1,2,3,4-tetrahydroisoquinoline hydrochloride, mp 252° C. (dec.).

(7) 1-(1,3,4-thiadiazol-2-yl)thiomethyl-6,7-dihydroxy-1,2,3,4-tetrahydroisoquinoline hydrochloride, mp 234° C. (dec.).

(8) 1-(2-benzothiazolyl)thiomethyl-6,7-dihydroxy-1,2,3,4-tetrahydroisoquinoline hydrochloride, mp 170° to 172° C.

(9) 1-(2-oxotetrahydrofuran-3-yl)thiomethyl-6,7-dihydroxy-1,2,3,4-tetrahydroisoquinoline hydrochloride, mp 236° to 239° C. (dec.).

(10) 1-(4-methylthiophenoxy)methyl-6,7-dihydroxy-1,2,3,4-tetrahydroisoquinoline hydrochloride, mp 270° C. (dec.).

(11) 1-(4-sulfamoylphenoxy)methyl-6,7-dihydroxy-1,2,3,4-tetrahydroisoquinoline hydrochloride, mp 270° C. (dec.).

EXAMPLE 3

(A) A mixture of 1-(1-methyl-1H-tetrazol-5-yl)-thiomethyl-6,7-dibenzyloxy-1,2,3,4-tetrahydroisoquinoline (300 mg) prepared by Example 2 (A), 99% ethanol (3 ml) and concentrated hydrochloric acid (3 ml) was refluxed for 3 hours. After the reaction, the solvent was distilled off, and to the residue was added ethanol. The solution was concentrated to dryness under reduced pressure and the residue was crystallized by adding acetone. The crystals were recrystallized from a mixture of ethanol and ether to give 1-(1-methyl-1H-tetrazol-5-yl)thiomethyl-6,7-dihydroxy-1,2,3,4-tetrahydroisoquinoline hydrochloride (220 mg), mp 215° to 216° C. (dec.).

(B) The following compounds were obtained by using the similar procedure to that of the above example, 3 (A).

(1) 1-(2-pyrimidinyl)thiomethyl-6,7-dihydroxy-1,2,3,4-tetrahydroisoquinoline hydrochloride, mp 204° to 205° C. (dec.).

(2) 1-(5-methyl-4H-1,2,4-triazol-3-yl)thiomethyl-6,7-dihydroxy-1,2,3,4-tetrahydroisoquinoline hydrochloride, mp 229° to 231° C. (dec.)

(3) 1-(2-thienyl)thiomethyl-6,7-dihydroxy-1,2,3,4-tetrahydroisoquinoline hydrochloride, mp 177° to 178° C.

(4) 1-(5-methyl-1,3,4-thiadiazol-2-yl)thiomethyl-6,7-dihydroxy-1,2,3,4-tetrahydroisoquinoline dihydrochloride, 199° to 201° C. (dec.).

(5) 1-(4-pyridyl)oxymethyl-6,7-dihydroxy-1,2,3,4-tetrahydroisoquinoline dihydrochloride, mp 250° to 255° C. (dec.).

(6) 1-(1,2,5-thiadiazol-3-yl)oxymethyl-6,7-dihydroxy-1,2,3,4-tetrahydroisoquinoline hydrochloride, mp 252° C. (dec.).

(7) 1-(1,3,4,-thiadiazol-2-yl)thiomethyl-6,7-dihydroxy-1,2,3,4-tetrahydroisoquinoline hydrochloride, mp 234° C. (dec.).

(8) 1-(2-benzothiazolyl)thiomethyl-6,7-dihydroxy-1,2,3,4-tetrahydroisoquinoline hydrochloride, mp 170° to 172° C.

(9) 1-(2-oxotetrahydrofuran-3-yl)thiomethyl-6,7-dihydroxy-1,2,3,4-tetrahydroisoquinoline hydrochloride, mp 236° to 239° C. (dec.).

(10) 1-(4-methylthiophenoxy)methyl-6,7-dihydroxy-1,2,3,4-tetrahydroisoquinoline hydrochloride, mp 270° C. (dec.).

(11) 1-(4-sulfamoylphenoxy)methyl-6,7-dihydroxy-1,2,3,4-tetrahydroisoquinoline hydrochloride, mp 270° C. (dec.).

EXAMPLE 4

(A) To a solution of 1-(4-chlorophenoxy)methyl-6-hydroxy-7-methoxy-1,2,3,4-tetrahydroisoquinoline (100 mg) in anhydrous methylene chloride (5 ml) was added boron tribromide (140 mg) at −60° C. under cooling and stirring, and then the reaction temperature was gradually elevated to at 15° C. over 22 hours. After the reaction, the reaction mixture was concentrated, and oily residue was dissolved in methanol (5 ml) and water (0.5 ml). The solution was refluxed for 10 minutes, and then the solvent was distilled off. The amorphous residue was dissolved in acetone, and to the solution was added ether, and the mixture was allowed to stand. The precipitated crystals were collected by filtration and dried to give 1-(4-chlorophenoxy)methyl-6,7-dihydroxy-1,2,3,4-tetrahydroisoquinoline hydrobromide (81 mg), mp 232° to 233° C. The product was identified with a sample by I.R. spectrum and N.M.R. spectrum.

(B) A mixture of 1-(4-chlorophenoxy)methyl-6-hydroxy-7-methoxy-1,2,3,4-tetrahydroisoquinoline (100 mg), lithium iodide trihydrate (150 mg) and benzoic acid (38 mg) was heated in an oil bath of 200° to 210° C. for 0.5 hour. After the reaction, the precipitated solid was dissolved in methanol absorbed with hydrogen chloride, and then insoluble material was filtered off. The filtrate was concentrated, and to the residue was added a small amount of ether, and the mixture was allowed to stand. The precipitated crystals were collected by filtration, and dried to give 1-(4-chlorophenoxy)methyl-6,7-dihydroxy-1,2,3,4-tetrahydroisoquinoline hydrochloride, mp 226° C. The product was identified with a sample by I.R. spectrum and N.M.R. spectrum.

(C) To a solution of 1-(4-chlorophenoxy)methyl-6,7-dimethoxy-1,2,3,4-tetrahydroisoquinoline (90 mg) in anhydrous methylene chloride (5 ml) was added boron tribromide (203 mg) at −55° C. under cooling and stirring, and then the reaction temperature was gradually elevated to at 5° C. over 17.5 hours. After the reaction, the reaction mixture was concentrated under reduced pressure. The residue was dissolved in methanol (5 ml) and water (0.5 ml), and the solution was warmed at 60° to 80° C. for 10 minutes and then the solution was concentrated. The amorphous residue was dissolved in acetone, and to the solution was added ether, and the mixture was allowed to stand. The precipitated crystals were collected by filtration and dried to give 1-(4-chlorophenoxy)methyl-6,7-dihydroxy-1,2,3,4-tetrahydroisoquinoline hydrobromide (77 mg), mp 232° to 233° C. The product was identified with a sample by I.R. spectrum and N.M.R. spectrum.

(D) A mixture of 1-(4-chlorophenoxy)methyl-6-hydroxy-7-methoxy-1,2,3,4-tetrahydroisoquinoline (100 mg), 47% hydrobromic acid (3 ml) and acetic acid (1.5 ml) was heated at 100° C. in an oil bath for 4.5 hours, and to the mixture was further added 47% hydrobromic acid (0.5 ml), and the mixture was continuously heated for 0.5 hour. After the reaction, the solvent was distilled off under reduced pressure. The amorphous residue was dissolved in acetone, and to the solution was added ether, and the mixture was allowed to stand. The precipitated crystals were collected by filtration to give 1-(4-chlorophenoxy)methyl-6,7-dihydroxy-1,2,3,4-tetrahydroisoquinoline hydrobromide (97 mg), mp 232° to 233° C. The product was identified with a sample by I.R. spectrum and N.M.R. spectrum.

(E) A suspension of 1-(4-chlorophenoxy)methyl-6,7-dimethoxy-1,2,3,4-tetrahydroisoquinoline hydrochloride (100 mg) in water was neutralized with concentrated aqueous ammonia solution, and then extracted with ethyl acetate. The extract was washed with water and dried, and then the solvent was distilled off under reduced pressure. Thus obtained 1-(4-chlorophenoxy)-methyl-6,7-dimethoxy-1,2,3,4-tetrahydroisoquinoline was dissolved in acetic acid (1.5 ml), and to the solution was added 47% hydrobromic acid (3 ml), and the mixture was heated in an oil bath of 100° C. for 4.5 hours. After the reaction, the solvent was distilled off under reduced pressure. The residue was dissolved in acetone (1 ml), and to the solution was added ether, and the mixture was allowed to stand overnight. The precipitated crystals were collected by filtration and recrystallized from a mixture of methanol and ether to give colourless crystals of 1-(4-chlorophenoxy)methyl-6,7-dihydroxy-1,2,3,4-tetrahydroisoquinoline hydrobromide, mp 230° to 232° C.

(F) To a solution of 1-(4-methoxyphenoxy)methyl-6,7-dimethoxy-1,2,3,4-tetrahydroisoquinoline (100 mg) in anhydrous methylene chloride (5 ml) was added a solution of boron tribromide (300 mg) in anhydrous methylene chloride (0.6 ml) at −51° C. under cooling and stirring, and the mixture was stirred for 10 hours at −51° to −20° C. After the reaction, methylene chloride was distilled off under reduced pressure. To the residue was added methanol (5 ml) and water (0.5 ml) and the mixture was warmed, and then the solvent was distilled off under reduced pressure. The colourless powderly residue was dissolved in acetone, and then to the solution was added ether, and the mixture was allowed to stand. The precipitated crystals were collected by filtration to give colourless powder of 1-(4-hydroxyphenoxy)methyl-6,7-dihydroxy-1,2,3,4-tetrahydroisoquinoline hydrobromide.

(G) The following compounds were obtained by using the similar procedure to those of the above examples, 4 (A) to 4 (F)

(1) 1-(4-chlorophenyl)thiomethyl-6,7-dihydroxy-1,2,3,4-tetrahydroisoquinoline hydrochloride, mp 200° to 203° C. (dec.).

(2) 1-(3,4-dichlorophenoxy)methyl-6,7-dihydroxy-1,2,3,4-tetrahydroisoquinoline hydrochloride, mp 99° C.

(3) 1-(4-hydroxyphenoxy)methyl-6,7-dihydroxy-1,2,3,4-tetrahydroisoquinoline hydrochloride, mp 262° C.

(4) 1-(3-trifluoromethylphenoxy)methyl-6,7-dihydroxy-1,2,3,4-tetrahydroisoquinoline hydrochloride, mp 233° to 235° C.

(5) 1-(4-nitrophenoxy)methyl-6,7-dihydroxy-1,2,3,4-tetrahydroisoquinoline hydrochloride, mp 238° to 240° C.

(6) 1-(4-aminophenoxy)methyl-6,7-dihydroxy-1,2,3,4-tetrahydroisoquinoline hydrochloride, mp 287° to 288° C.

(7) 1-(4-hydroxyphenoxy)methyl-3-methyl-6,7-dihydroxy-1,2,3,4-tetrahydroisoquinoline hydrochloride, mp 156° C.

(8) 1-(3-hydroxyphenoxy)methyl-6,7-dihydroxy-1,2,3,4-tetrahydroisoquinoline hydrochloride, mp 252° to 254° C.

(9) 1-(2-hydroxyphenoxy)methyl-6,7-dihydroxy-1,2,3,4-tetrahydroisoquinoline hydrochloride, mp 239° to 241° C.

(10) 1-(4-hydroxyphenyl)thiomethyl-6,7-dihydroxy-1,2,3,4-tetrahydroisoquinoline hydrochloride, amorphous.

(11) 1-(2-fluorophenyl)thiomethyl-6,7-dihydroxy-1,2,3,4-tetrahydroisoquinoline hydrochloride, mp 193° to 195° C.

(12) 1-(4-fluorophenyl)thiomethyl-6,7-dihydroxy-1,2,3,4-tetrahydroisoquinoline hydrochloride, mp 104° to 107° C.

(13) 1-(4-hydroxyphenoxy)methyl-2-methyl-6,7-dihydroxy-1,2,3,4-tetrahydroisoquinoline hydrochloride, mp 231° to 232° C.

(14) 1-(2-chlorophenyl)thiomethyl-6,7-dihydroxy-1,2,3,4-tetrahydroisoquinoline hydrochloride, mp 249° to 251° C.

(15) 1-(4-fluorophenoxy)methyl-6,7-dihydroxy-1,2,3,4-tetrahydroisoquinoline hydrochloride, mp 93° to 95° C.

(16) 1-(3-chlorophenoxy)methyl-6,7-dihydroxy-1,2,3,4-tetrahydroisoquinoline hydrochloride, mp 244° to 245° C.

(17) 1-(4-biphenylyl)oxymethyl-6,7-dihydroxy-1,2,3,4-tetrahydroisoquinoline hydrochloride, mp 242° to 245° C. (dec.).

(18) 1-(4-phenoxyphenoxy)methyl-6,7-dihydroxy-1,2,3,4-tetrahydroisoquinoline hydrochloride, mp 222° to 223.5° C.

(19) 1-(4-dimethylaminophenyl)thiomethyl-6,7-dihydroxy-1,2,3,4-tetrahydroisoquinoline hydrochloride, amorphous.

(20) 1-(4-methanesulfonamidophenoxy)methyl-6,7-dihydroxy-1,2,3,4-tetrahydroisoquinoline hydrochloride, mp 253° to 255° C.

(21) 1-(4-methylthiophenoxy)methyl-6,7-dihydroxy-1,2,3,4-tetrahydroisoquinoline hydrochloride, mp 270° C. (dec.).

(22) 1-(4-sulfamoylphenoxy)methyl-6,7-dihydroxy-1,2,3,4-tetrahydroisoquinoline hydrochloride, mp 270° C. (dec.).

(H) A solution of boron tribromide (2.4 g) in dried methylene chloride (5 ml) was dropwise added at −60° C. to a solution of 1-(1-methyl-1H-tetrazol-5-yl)thiomethyl-6.7-dimethoxy-1,2,3,4-tetrahydroisoquinoline (0.5 g) obtained by Example 2 (C) in dried methylene chloride (10 ml). The reaction temperature was elevated to room temperature over one night. Methanol (5 ml) was added to the reaction mixture under ice-cooling and the mixture was concentrated under reduced pressure. The residual oil was crystallized by treating with ethanol, and the crystals were collected by filtration to give 1-(1-methyl-1H-tetrazol-5-yl)-thiomethyl-6,7-dihydroxy-1,2,3,4-tetrahydroisoquinoline hydrobromide (0.25 g). The crystals were converted into their hydrochloride by a conventional manner and recrystallized from a mixture of ethanol and ether to give colorless crystals of 1-(1-methyl-1H-tetrazol-5-yl)-thiomethyl-6,7-dihydroxy-1,2,3,4-tetrahydroisoquinoline hydrochloride, mp 215° to 216° C. (dec.).

(I) The following compounds were obtained by using the similar procedure to those of the above examples, 4(A) to 4(F) and 4(H).

(1) 1-(2-pyrimidinyl)thiomethyl-6,7-dihydroxy-1,2,3,4-tetrahydroisoquinoline hydrochloride, mp 204° to 205° C. (dec.).

(2) 1-(5-methyl-4H-1,2,4-triazol-3-yl)thiomethyl-6,7-dihydroxy-1,2,3,4-tetrahydroisoquinoline hydrochloride, mp 229° to 231° 1 C. (dec.).

(3) 1-(2-thienyl)thiomethyl-6,7-dihydroxy-1,2,3,4-tetrahydroisoquinoline hydrochloride, mp 177° to 178° C.

(4) 1-(5-methyl-1,3,4-thiadiazol-2-yl)thiomethyl-6,7-dihydroxy-1,2,3,4-tetrahydroisoquinoline dihydrochloride, 199° to 201° C. (dec.).

(5) 1-(4-pyridyl)oxymethyl-6,7-dihydroxy-1,2,3,4-tetrahydroisoquinoline dihydrochloride, mp 250° to 255° C. (dec.).

(6) 1-(1,2,5-thiadiazol-3-yl)oxymethyl-6,7-dihydroxy-1,2,3,4-tetrahydroisoquinoline hydrochloride, mp 252° C. (dec.).

(7) 1-(1,3,4-thiadiazol-2-yl)thiomethyl-6,7-dihydroxy-1,2,3,4-tetrahydroisoquinoline hydrochloride, mp 234° C. (dec.).

(8) 1-(2-benzothiazolyl)thiomethyl-6,7-dihydroxy-1,2,3,4-tetrahydroisoquinoline hydrochloride, m.p. 170° to 172° C.

(9) 1-(2-oxotetrahydrofuran-3-yl)thiomethyl-6,7-dihydroxy-1,2,3,4-tetrahydroisoquinoline hydrochloride, mp 236° to 239° C. (dec.).

EXAMPLE 5

(I)

(1) A suspension of 1-(1-methyl-1H-tetrazol-5-yl)thiomethyl-6,7-dihydroxy-1,2,3,4-tetrahydroisoquinoline hydrochloride (50 g) in water (300 ml) was dissolved at 61° to 65° C. To the solution was added sodium bicarbonate (13.3 g) over 15 minutes at the same temperature. Tetrahydrofuran (250 ml) was added to the suspension at 50° C. The suspension was cooled and weakly alkalified by adding sodium bicarbonate (30 g) at 0° to 3° C. To the mixture was added 2,2,2-trichloroethyl chloroformate (40.2 g) over 30 minutes below 3° C. The resulting mixture was stirred for 30 minutes at 0° C. Water (300 ml) was added to the reaction mixture and the mixture was twice extracted with ethyl acetate (900 ml and 600 ml). The extract was washed with a sodium chloride aqueous solution (300 ml) and dried over magnesium sulfate. The solvent was distilled off under reduced pressure and the residue was crystallized with ether to give 1-(1-methyl-1H-tetrazol-5-yl)thiomethyl-2-(2,2,2-trichloroethoxycarbonyl)-6,7-dihydroxy-1,2,3,4-tetrahydroisoquinoline (40.4 g), mp 201° to 207° C.

I.R. spectrum (Nujol) 1690, 1720 cm$^{-1}$
N.M.R. spectrum (d$_6$-DMSO, δ)
ppm　　　　2.3 ~ 4.3(6H, m)
　　　　　　3.86(3H, s)
　　　　　　4.75(2H, ABq)
　　　　4.9 ~ 5.5 (1H, m)
　　　　　　6.70(1H, s)
　　　　　　6.78(1H, s)
　　　　　　8.9 (2H, broad s)

(2) The following compounds were obtained according to a similar manner to that of Example 5 (I) (1).

(i) 1-(2-Thienyl)thiomethyl-2-(2,2,2-trichloroethoxycarbonyl)-6,7-dihydroxy-1,2,3,4-tetrahydroisoquinoline. mp 186° to 194° C.

I.R. spectrum (Nujol) 1695 cm$^{-1}$
N.M.R. spectrum (d$_4$-DMSO, δ)
ppm　　2.5 ~ 4.2(6H, m), 4.9(2H, s)
　　　　4.9 ~ 5.2(1H, m), 6.6(2H, s)
　　　　6.9 ~ 7.8(3H, m), 8.8(2H, broad s)

(ii) 1-(2-Benzothiazolyl)thiomethyl-2-(2,2,2-trichloroethoxycarbonyl)-6,7-dihydroxy-1,2,3,4-tetrahydroisoquinoline.
Colorless crystals I.R. spectrum (Nujol) 1690 cm$^{-1}$ -continued N.M.R. spectrum (d₄-DMSO, δ)
ppm   2.4 ~ 4.2(6H, m), 4.4 ~ 5.0(2H, m),
      5.3 ~ 5.7(1H, m), 6.5 ~ 8.2(6H, m),
      9.0(2H, s)

(iii) 1-(5-Methyl-1,3,4-thiadiazol-2-yl)thiomethyl-2-(2,2,2-trichloroethoxycarbonyl)-6,7-dihydroxy-1,2,3,4-tetrahydroisoquinoline. mp 172° to 186° C.

I.R. spectrum (Nujol)
1700 cm⁻¹
N.M.R. spectrum (d₄-DMSO, δ)
ppm   2.8(3H, s), 3.2 ~ 4.4(6H, m),
      4.7 ~ 5.2(2H, m), 5.2 ~ 5.6(1H, m),
      6.7(1H, s), 6.85(1H, s), 82(2H, broad s)

(II)

(1) A mixture of 1-(2-thienyl)thiomethyl-2-(2,2,2-trichloroethoxycarbonyl)-6,7-dihydroxy-1,2,3,4-tetrahydroisoquinoline (10 g) and acetic anhydride (20 ml) was stirred for 1 hour at 130° C. The reaction mixture was poured into ice-water (100 ml) and the resulting mixture was twice extracted with ethyl acetate (100 ml and 50 ml). The combined extract was in turn washed four times with a saturated aqueous solution of sodium bicarbonate (50 ml) and once with a saturated aqueous solution of sodium chloride (50 ml) and dried over magnesium sulfate. The solvent was distilled off under reduced pressure to give oil (13.2 g). The oil was purified by subjecting to column chromatography on silica gel (200 g) using a mixture of benzene and ethyl acetate (5:1) as a developing solvent to give oil of 1-(2-thienyl)thiomethyl-2-(2,2,2-trichloroethoxycarbonyl)-6,7-bisacetoxy-1,2,3,4-tetrahydroisoquinoline (6.9 g).

I.R. spectrum (Film)
1770, 1720 cm⁻¹
N.M.R. spectrum (CDCl₃, δ)
ppm   2.2 (6H, s)
      2.7 ~ 4.4(6H, m)
      4.75(2H, ABq)
      5.35(1H, t)
      6.8 ~ 7.4(5H, m)

(2) 2-Thenoyl chloride (7.5 g) was dropwise added over 10 minutes at 10° C. to a solution of 1-(1-methyl-1H-tetrazol-5-yl)thiomethyl-2-(2,2,2-trichloroethoxycarbonyl)-6,7-dihydroxy-1,2,3,4-tetrahydroisoquinoline (10 g) and sodium hydroxide (2 g) in a mixture of water (100 ml) and tetrahydrofuran (60 ml). The resulting mixture was stirred for 1.5 hours at the same temperature and for 1 hour at room temperature adjusting the solution to alkaline condition by adding a dilute aqueous solution of sodium hydroxide. The reaction mixture was poured into water (100 ml) and the resulting mixture was twice extracted with ethyl acetate (200 ml and 100 ml). The combined extract was washed with a saturated aqueous solution of sodium chloride (100 ml) and dried over magnesium sulfate. The solvent was distilled off to give oil (16.5 g). The oil was subjected to column chromatography on silica gel (240 g). The column was washed with benzene (1 l) and the oil was eluted with a mixture of benzene and ethyl acetate (5:1). The eluate containing the object compound was concentrated to give 1-(1-methyl-1H-tetrazol-5-yl)thiomethyl-2-(2,2,2-trichloroethoxycarbonyl)-6,7-bis(2-thenoyloxy)-1,2,3,4-tetrahydroisoquinoline (7.3 g). mp 139° to 146° C.

I.R. spectrum (Nujol)
1740, 1695 cm⁻¹
N.M.R. spectrum (CDCl₃, δ)
ppm   2.7 ~ 4.6(6H, m)
      3.8(3H, s)
      4.8(2H, ABq)
      5.3 ~ 5.9(1H, m)
      6.9 ~ 7.9(3H, m), (3) The following compounds were obtained according to similar manners to those of Examples 5 (II) (1) and 5 (II) (2). (i) 1-(2-Benzothiazolyl)thiomethyl-2-(2,2,2-trichloroethoxycarbonyl)-6,7-bisacetoxy-1,2,3,4-tetrahydroisoquinoline. mp 145° to 147° C.

I.R. spectrum (Nujol)
1780 1760 1700 cm⁻¹
N.M.R. spectrum (d₆-DMSO, δ)
ppm   2.28(3H, s), 2.30(3H, s),
      2.7 ~ 4.3(6H, m), 4.6 ~ 4.9(2H, m)
      5.5 ~ 5.8(1H, m), 7.1 ~ 8.1(6H, m)

(ii) 1-(2-Benzothiazolyl)thiomethyl-2-(2,2,2-trichloroethoxycarbonyl)-6,7-bis(phenylacetoxy)-1,2,3,4-tetrahydroisoquinoline. Oil.

I.R. spectrum (CHCl₃)
1765, 1715 cm⁻¹
N.M.R. spectrum (CDCl₃, δ)
ppm   2.7 ~ 4.3(6H, m), 3.55(2H, s),
      3.58(2H, s), 4.6 ~ 4.8(2H, m),
      5.5 ~ 5.9(1H, m), 6.9 ~ 7.8(16H, m)

(iii) 1-(5-Methyl-1,3,4-thiadiazol-2-yl)thiomethyl-2-(2,2,2-trichloroethoxycarbonyl)-6,7-bisacetoxy-1,2,3,4-tetrahydroisoquinoline. mp 146° to 150° C.

I.R. spectrum (Nujol)
1765, 1710 cm⁻¹
N.M.R. spectrum (CDCl₃, δ)
ppm   2.3(6H, s), 2.7 ~ 4.4(6H, m),
      2.75(3H, s), 4.8(2H, ABq),
      5.5 ~ 5.9(1H, m), 7.00(1H, s),
      7.30(1H, s)

(iv) 1-(5-Methyl-1,3,4-thiadiazol-2-yl)thiomethyl-2-(2,2,2-trichloroethoxycarbonyl)-6,7-bis(2-thienylacetoxy)-1,2,3,4-tetrahydroisoquinoline. Oil.

I.R. spectrum (Film)
1770, 1720 cm⁻¹
N.M.R. spectrum (d₄-DMSO, δ)
ppm   2.7(3H, s), 2.7 ~ 4.3(6H, m)
      4.08(2H, s), 4.13(2H, s),
      4.7 ~ 5.0(2H, m), 5.4 ~ 5.8(1H, m),
      6.9 ~ 7.6(3H, m)

(v) 1-(2-Thienyl)thiomethyl-2-(2,2,2-trichloroethoxycarbonyl)-6,7-bispalmitoyloxy-1,2,3,4-tetrahydroisoquinoline. mp 55° to 61° C.

I.R. spectrum (Nujol)
1770, 1710 cm⁻¹
N.M.R. spectrum (CDCl₃, δ)
ppm   0.7 ~ 2.1(62H, m), 2.3 ~ 3.7(6H, m), 4.9(2H, ABq), 5.4(1H, t),
6.8 ~ 7.5(5H, m)

(vi) 1-(1-Methyl-1H-tetrazol-5-yl)thiomethyl-2-(2,2,2-trichloroethoxycarbonyl)-6,7-bisacetoxy-1,2,3,4-tetrahydroisoquinoline. mp 199° to 202° C.

| I.R. spectrum (Nujol) |
|---|
| 1770, 1710 cm$^{-1}$ |
| N.M.R. spectrum (CDCl$_3$, δ) |
| ppm    2.30(3H, s), 2.32(3H, s), |
| 2.7 ~ 4.6(6H, m), 3.90(3H, s) |
| 4.85(2H, ABq), 5.4 ~ 5.9(1H, m), |
| 7.03(1H, s), 7.42(1H, s) |

(vii) 1-(1-Methyl-1H-tetrazol-5-yl) thiomethyl-2-(2,2,2-trichloroethoxycarbonyl)-6,7-bisbenzoyloxy-1,2,3,4-tetrahydroisoquinoline. Crystals.

| I.R. spectrum (Nujol) |
|---|
| 1750, 1730, 1695 cm$^{-1}$ |
| N.M.R. spectrum (d$_4$-DMSO, δ) |
| ppm    2.7 ~ 4.3(6H, m), 4.0(3H, s), |
| 4.9(2H, broad s), 5.4 ~ 6.0(1H, m), |
| 7.4 ~ 8.2(12H, m) |

(viii) 1-(1-Methyl-1H-tetrazol-5-yl)thiomethyl-2-(2,2,2-trichloroethoxycarbonyl)-6,7-bisisobutyryloxy-1,2,3,4-tetrahydroisoquinoline. Crystals.

| I.R. spectrum (Nujol) |
|---|
| 1770, 1725 cm$^{-1}$ |
| N.M.R. spectrum (d$_4$-DMSO, δ) |
| ppm    1.2(12H, d), 2.6 ~ 4.3(6H, m), |
| 2.6 ~ 2.9(2H, m), 3.9(3H, s), |
| 4.7 ~ 4.9(2H, m), 5.3 ~ 5.7(1H, m), |
| 7.08(1H, s), 7.30(1H, s) |

(III)

(1) Zinc powder (6.9 g) was added to a solution of 1-(2-thienyl)thiomethyl-2-(2,2,2-trichloroethoxycarbonyl)-6,7-bisacetoxy-1,2,3,4-tetrahydroisoquinoline (6.9 g) in acetic acid (40 ml) at 62° C. and the resulting mixture was stirred for 1 hour at the same temperature. The reaction mixture was filtered and the filtrate was concentrated. Water (100 ml) was added to the residue and the mixture was twice extracted with ethyl acetate (150 ml and 50 ml). The combined extract was in turn washed three times with a saturated aqueous solution of sodium bicarbonate (50 ml) and once with a saturated aqueous solution of sodium chloride (50 ml) and then dried over magnesium sulfate. The solvent was distilled off under reduced pressure to give oil (4.4 g). The oil was dissolved in acetone (150 ml) and fumaric acid (1.5 g) was added thereto and dissolved by warming. The solution was concentrated at room temperature to give crystals of 1-(2-thienyl)thiomethyl-6,7-bisacetoxy-1,2,3,4-tetrahydroisoquinoline fumarate (3.3 g). mp 105° to 109° C.

| I.R. spectrum (Nujol) |
|---|
| 1770, 1695 cm$^{-1}$ |
| N.M.R. spectrum (d$_6$-DMSO, δ) |
| ppm    2.3(6H, s), 2.6 ~ 3.5(6H, m), |
| 4.1 ~ 4.4(1H, m), 6.6(2H, s), |
| 7 ~ 7.8(5H, m), 9.8(3H, broad s) |

(2) 1-(1-Methyl-1H-tetrazol-5-yl)thiomethyl-2-(2,2,2-trichloroethoxycarbonyl)-6,7-bisacetoxy-1,2,3,4-tetrahydroisoquinoline (8 g) was dissolved in a mixture of acetic acid (50 ml) and formic acid (50 ml) at 83° C. Zinc powder (4 g) was added thereto with stirring at the same temperature and the mixture was stirred for 30 minutes at the same temperature. The reaction mixture was filtered and the filtrate was concentrated to give oily residue. Water (150 ml) was added to the residue and the mixture was washed with ethyl acetate. To the aqueous layer was added an aqueous solution of sodium carbonate and the mixture was three times extracted with ethyl acetate (100 ml, 50 ml and 50 ml). The combined extract was washed with a saturated aqueous solution of sodium chloride (50 ml), dried over magnesium sulfate and concentrated to give oil (4.5 g). The oil was dissolved in ethyl acetate (150 ml) and fumaric acid (1.4 g) was added thereto. After stirring under warming, the mixture was allowed to stand for 2 days. Precipitates were collected by filtration to give crystals of 1-(1-methyl-1H-tetrazol-5-yl)thiomethyl-6,7-bisacetoxy-1,2,3,4-tetrahydroisoquinoline fumarate (5.25 g). mp 139° to 143° C. The crystals were recrystallized from a mixture of ethanol (50 ml) and acetone (150 ml) to give pure compound (3.7 g). mp 134° to 136° C.

| I.R. spectrum (Nujol) |
|---|
| 1770, 1710 cm$^{-1}$ |
| N.M.R. spectrum (d$_6$-DMSO, δ) |
| ppm    2.22(3H, s) |
| 2.26(3H, s) |
| 2.6 ~ 3.2(4H, m) |
| 3.6 ~ 3.9(2H, m) |
| 3.90(3H, s) |
| 4.3 ~ 4.5(1H, m) |
| 6.55(2H, s) |
| 7.13(1H, s) |
| 7.22(1H, s) |
| 8.5(3H, broad s) |

(3) The following compounds were obtained according to similar manners to those of Examples 5 (III) (1) and 5 (III) (2).

(i) 1-(2-Benzothiazolyl)thiomethyl-6,7-bisacetoxy-1,2,3,4-tetrahydroisoquinoline hemifumarate. mp 172° to 173° C.

| I.R. spectrum (Nujol) |
|---|
| 1780, 1690 cm$^{-1}$ |
| N.M.R. spectrum (d$_4$-DMSO, δ) |
| ppm    2.3(6H, s), 2.8 ~ 4.2(6H, m), |
| 5.35(1H, t), 6.8(1H, s), |
| 7 ~ 7.9(6H, m) |

(ii) 1-(2-Benzothiazolyl)thiomethyl-6,7-bis(phenylacetoxy)-1,2,3,4-tetrahydroisoquinoline. mp 153° to 155° C.

| I.R. spectrum (Nujol) |
|---|
| 1770 cm$^{-1}$ |
| N.M.R. spectrum (d$_6$-DMSO, δ) |
| ppm    2.3(1H, t), 2.8 ~ 3.3(4H, m), |
| 3.6 ~ 4.1(2H, m), 3.8(4H, s), |

-continued

| 5.3(1H, t), 7 ~ 7.9(16H, m) |

(iii) 1-(5-Methyl-1,3,4-thiadiazol-2-yl)thiomethyl-6,7-bisacetoxy-1,2,3,4-tetrahydroisoquinoline hemitartrate. mp 187° to 191° C.

| I.R. spectrum (Nujol) |
| 1775 cm$^{-1}$ |
| N.M.R. spectrum (d$_6$-DMSO, δ) |
| ppm  2.3(9H, s), 2.6 ~ 4.6(6H, m), |
|      4.9 ~ 5.4(1H, m), 7.10(1H, s), |
|      7.15(1H, s) |

(iv) 1-(5-Methyl-1,3,4-thiadiazol-2-yl)thiomethyl-6,7-bis(2-thienylacetoxy)-1,2,3,4-tetrahydroisoquinoline. mp 210° to 212° C.

| I.R. spectrum (Nujol) |
| 1775 cm$^{-1}$ |
| N.M.R. spectrum (d$_6$-DMSO, δ) |
| ppm  2.3(3H, s), 2.6 ~ 4.6(6H, m), |
|      4.1(4H, s), 4.9 ~ 5.3(1H, m), |
|      6.9 ~ 7.6(8H, m) |

(v) 1-(2-Thienyl)thiomethyl-6,7-bispalmitoyloxy-1,2,3,4-tetrahydroisoquinoline fumarate. mp 123° to 125° C.

| I.R. spectrum (Nujol) |
| 1770, 1710 cm$^{-1}$ |
| N.M.R. spectrum (d$_6$-DMSO, δ) |
| ppm  0.7 ~ 1.8(62H, m), 2.6 ~ 3.3(6H, m) |
|      5.4(3H, s), 6.6(2H, s), 6.7 ~ 7.5(5H, m) |

(vi) 1-(1-Methyl-1H-tetrazol-5-yl)thiomethyl-6,7-bis(2-thenoyloxy)-1,2,3,4-tetrahydroisoquinoline fumarate. mp 110° to 113° C.

| I.R. spectrum (Nujol) |
| 1730, 1690 cm$^{-1}$ |
| N.M.R. spectrum (d$_6$-DMSO, δ) |
| ppm  2.6 ~ 3.4(4H, m), 3.8 ~ 4.2(2H, m), |
|      4.0(3H, s), 4.3 ~ 4.8(1H, m), |
|      6.7(2H, s), 7.2 ~ 8.2(8H, m), |
|      7.7(3H, s) |

(vii) 1-(1-Methyl-1H-tetrazol-5-yl)thiomethyl-6,7-bisbenzoyloxy-1,2,3,4-tetrahydroisoquinoline hemifumarate. mp 165° to 167° C.

| I.R. spectrum (Nujol) |
| 1740 cm$^{-1}$ |
| N.M.R. spectrum (d$_6$-DMSO, δ) |
| ppm  2.7 ~ 3.4(4H, m), 3.7 ~ 4.2(2H, m), |
|      3.9(3H, s), 4.4 ~ 4.6(1H, m), |
|      6.55(2H, s), 6.7(1H, s), |
|      7.3 ~ 8.2(12H, m) |

(viii) 1-(1-Methyl-1H-tetrazol-5-yl)thiomethyl-6,7-bisisobutyryloxy-1,2,3,4-tetrahydroisoquinoline fumarate. mp 175° to 177° C.

| I.R. spectrum (Nujol) |
| 1770, 1710 cm$^{-1}$ |
| N.M.R. spectrum (d$_6$-DMSO, δ) |
| ppm  1.15(12H, d), 2.6 ~ 3.4(4H, m), |
|      2.8(2H, q), 3.7 ~ 4.0(2H, m), |
|      3.9(3H, s), 4.3 ~ 4.6(1H, m), |
|      6.6(2H, s), 7.05(1H, s), |
|      7.25(1H, s), 8.3(3H, broad s) |

What we claim is:

1. A 1,2,3,4-tetrahydroisoquinoline having the formula:

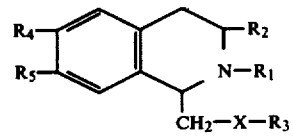

wherein $R_1$ and $R_2$ are each hydrogen or lower alkyl, $R_3$ is thiadiazolyl optionally substituted by lower alkyl, $R_4$ and $R_5$ are each hydroxy or protected hydroxy and X is —O— or —S— and pharmaceutically acceptable salts thereof.

2. The compound of claim 1, wherein $R_3$ is 5-methyl-1,3,4-thiadiazol-2-yl, X is —S— or its dihydrochloride.

3. The compound of claim 1, wherein $R_3$ is 1,2,5-thiadiazol-3-yl, X is —O— or its hydrochloride.

4. The compound of claim 1, wherein $R_3$ is 1,3,4-thiadiazol-2-yl, X is —S— or its hydrochloride.

5. The compound of claim 1, wherein $R_3$ is 5-methyl-1,3,4-thiadiazol-2-yl, $R_4$ and $R_5$ are both acetoxy or its hemitartrate.

6. The compound of claim 1, wherein $R_3$ is 5-methyl-1,3,4-thiadiazol-2-yl and $R_4$ and $R_5$ are both 2-thienylacetoxy.

7. A 1,2,3,4-tetrahydroisoquinoline having the formula:

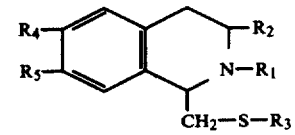

wherein $R_1$ and $R_2$ are each hydrogen or lower alkyl, $R_3$ is thiadiazol-2-yl, $R_4$ and $R_5$ are each hydroxy or protected hydroxy and pharmaceutically acceptable salts thereof.

8. A pharmaceutical composition comprising, as an active ingredient, at least one 1,2,3,4-tetrahydroisoquinoline having the formula:

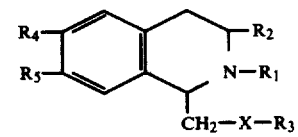

wherein $R_1$ and $R_2$ are each hydrogen or lower alkyl, $R_3$ is thiadiazolyl optionally substituted by a lower alkyl group, $R_4$ and $R_5$ are each hydroxy or a protected hydroxy and X is —O— or —S—, and pharmaceutically acceptable salts thereof, with a pharmaceutically acceptable carrier.